(12) United States Patent
Stürzebecher et al.

(10) Patent No.: US 9,365,613 B2
(45) Date of Patent: Jun. 14, 2016

(54) ACYLATED 4-AMIDINO- AND -4-GUANIDINOBENZYLAMINES FOR INHIBITION OF PLASMA KALLIKREIN

(75) Inventors: Jörg Stürzebecher, Erfurt (DE); Torsten Steinmetzer, Jena (DE); Andrea Schweinitz, Jena (DE)

(73) Assignee: The Medicines Company (Leipzig) GmbH, Leipzig (DE)

( * ) Notice: Subject to any disclaimer, the term of this patent is extended or adjusted under 35 U.S.C. 154(b) by 1151 days.

(21) Appl. No.: 10/540,958

(22) PCT Filed: Jan. 15, 2004

(86) PCT No.: PCT/EP2004/000247
§ 371 (c)(1),
(2), (4) Date: Jan. 3, 2006

(87) PCT Pub. No.: WO2004/062657
PCT Pub. Date: Jul. 29, 2004

(65) Prior Publication Data
US 2006/0148901 A1 Jul. 6, 2006

(30) Foreign Application Priority Data
Jan. 15, 2003 (DE) .................................. 103 01 300

(51) Int. Cl.
*A01N 43/00* (2006.01)
*A61K 31/33* (2006.01)
*A01N 37/12* (2006.01)
*A01N 37/44* (2006.01)
*C07K 5/072* (2006.01)
*A61K 31/198* (2006.01)
*A61K 31/401* (2006.01)
*A61K 31/435* (2006.01)
*A61K 47/48* (2006.01)
*C07K 5/062* (2006.01)
*C07K 5/065* (2006.01)

(52) U.S. Cl.
CPC ........... *C07K 5/06095* (2013.01); *A61K 31/198* (2013.01); *A61K 31/401* (2013.01); *A61K 31/435* (2013.01); *A61K 47/48215* (2013.01); *C07K 5/0606* (2013.01); *C07K 5/06034* (2013.01); *C07K 5/06078* (2013.01)

(58) Field of Classification Search
CPC ........... C07K 5/06095; C07K 5/06034; A61K 31/198; A61K 47/48215
USPC .................................................. 514/183, 562
See application file for complete search history.

(56) References Cited

U.S. PATENT DOCUMENTS

| | | | |
|---|---|---|---|
| 5,518,735 A | 5/1996 | Stürzebecher et al. | |
| 5,602,253 A | 2/1997 | Antonsson et al. | |
| 5,705,487 A | 1/1998 | Schacht et al. | |
| 5,707,966 A | 1/1998 | Schacht et al. | |
| 5,710,130 A | 1/1998 | Schacht et al. | |
| 5,726,159 A | 3/1998 | Schacht et al. | |
| 5,863,929 A | 1/1999 | Klimkowski et al. | |
| 5,914,319 A | 6/1999 | Schacht et al. | |
| 6,030,972 A | 2/2000 | Böhm et al. | |
| 6,472,393 B1 | 10/2002 | Aliagas-Martin et al. | |
| 6,586,405 B2 | 7/2003 | Semple et al. | |
| 6,624,169 B1 | 9/2003 | Wilhelm et al. | |
| 6,831,196 B2 | 12/2004 | Stürzebecher et al. | |
| 6,841,701 B2 | 1/2005 | Sturzebecher et al. | |
| 6,841,702 B2 | 1/2005 | Magdolen et al. | |
| 7,038,074 B2 | 5/2006 | Moroder et al. | |
| 7,049,460 B1 | 5/2006 | Magdolen et al. | |
| 7,208,521 B2 | 4/2007 | Magdolen et al. | |
| 7,407,982 B2 | 8/2008 | Steinmetzer et al. | |
| 7,538,216 B2 | 5/2009 | Sperl | |
| 7,608,623 B2 | 10/2009 | Sperl et al. | |
| 7,772,251 B2 | 8/2010 | Sturzebecher et al. | |
| 7,838,560 B2 | 11/2010 | Sturzebecher et al. | |
| 8,124,587 B2 | 2/2012 | Steinmetzer et al. | |

(Continued)

FOREIGN PATENT DOCUMENTS

| CA | 2412181 | 12/2002 |
|---|---|---|
| CH | 689 611 | 7/1999 |

(Continued)

OTHER PUBLICATIONS

Akers (Journal of Pharmaceutical sciences (2002) 91:2283-2300).*
Lee et. al. (Bioorganic and medicinal Chemistry Letters (2002) 1017-1022).*
Asghar et al., "Human Plasma Kallikreins and their Inhibition by Amidino Compounds," *Biochim. Biophys. Acta* 438:250-264 (1976).
Baker et al., "Inhibition of Cancer Cell Urokinase Plasminogen Activator by its Specific Inhibitor PAI-2 and Subsequent Effects on Extracellular matrix Degradation," *Cancer Research* 50: 4676-4684 (1990).

(Continued)

*Primary Examiner* — Marcos Sznaidman
(74) *Attorney, Agent, or Firm* — Clark & Elbing LLP

(57) ABSTRACT

The invention relates to the use of acylated 4-amidino- or 4-guanidinobenzylamine in accordance with the general formula I

P4-P3-P2-P1                                (I), where P4 is a monosubstituted or polysubstituted or unsubstituted benzylsulfonyl group, P3 is a monosubstituted or polysubstituted or unsubstituted, natural or unnatural α-amino acid or α-imino acid in the D configuration, P2 is a monosubstituted or polysubstituted or unsubstituted, natural or unnatural α-amino acid or α-imino acid in the L configuration, and P1 is a monosubstituted or polysubstituted or unsubstituted 4-amidino- or 4-guanidinobenzylamine group, for inhibiting plasma kallikrein (PK), factor XIa and factor XIIa, in particular for preventing the activation of coagulation at synthetic surfaces and for systemic administration as anticoagulants/antithrombotic agents, in particular for preventing the activation of coagulation at synthetic surfaces for the purpose of averting thromboembolic events.

10 Claims, No Drawings

(56) References Cited

U.S. PATENT DOCUMENTS

| | | | |
|---|---|---|---|
| 8,207,378 | B2 | 6/2012 | Steinmetzer et al. |
| 8,410,310 | B2 | 4/2013 | Steinmetzer et al. |
| 8,497,245 | B2 | 7/2013 | Herold et al. |
| 8,513,461 | B2 | 8/2013 | Steinmetzer et al. |
| 8,921,319 | B2 | 12/2014 | Steinmetzer et al. |
| 2002/0037857 | A1 | 3/2002 | Semple et al. |
| 2004/0266766 | A1 | 12/2004 | Sperl |
| 2005/0119190 | A1 | 6/2005 | Stürzebecher et al. |
| 2005/0176993 | A1 | 8/2005 | Stürzebecher et al. |
| 2006/0068457 | A1 | 3/2006 | Ziegler et al. |
| 2007/0055065 | A1 | 3/2007 | Stürzebecher et al. |
| 2007/0066539 | A1 | 3/2007 | Stürzebecher et al. |
| 2008/0261998 | A1 | 10/2008 | Sperl et al. |
| 2009/0117185 | A1 | 5/2009 | Steinmetzer et al. |
| 2010/0022781 | A1 | 1/2010 | Steinmetzer et al. |

FOREIGN PATENT DOCUMENTS

| | | | |
|---|---|---|---|
| DE | 42 43 858 | | 6/1994 |
| DE | 101 02 878 | A1 | 8/2001 |
| DE | 100 29 014 | | 12/2001 |
| DE | 100 29 015 | | 12/2001 |
| DE | 102 10 590 | | 3/2002 |
| DE | 102 12 555 | | 9/2003 |
| DE | 103 01 300 | | 7/2004 |
| EP | 0 183 271 | | 6/1986 |
| EP | 0 669 317 | | 8/1995 |
| EP | 0 672 658 | | 9/1995 |
| EP | 1 364 960 | | 11/2003 |
| WO | WO 92/08709 | | 5/1992 |
| WO | WO 94/18185 | | 8/1994 |
| WO | WO 94/29336 | | 12/1994 |
| WO | WO 95/17885 | | 7/1995 |
| WO | WO 95/29189 | | 11/1995 |
| WO | WO 96/25426 | | 8/1996 |
| WO | WO 97/23499 | | 7/1997 |
| WO | WO 99/05096 | | 2/1999 |
| WO | WO 00/04954 | | 2/2000 |
| WO | WO 00/05245 | | 2/2000 |
| WO | WO 00/14110 | | 3/2000 |
| WO | WO 00/17158 | | 3/2000 |
| WO | WO0058346 | * | 5/2000 |
| WO | WO 00/58346 | | 10/2000 |
| WO | WO 00/64470 | | 11/2000 |
| WO | WO 01/81314 | | 11/2001 |
| WO | WO 01/96286 | | 12/2001 |
| WO | WO 01/96366 | * | 12/2001 |
| WO | WO 01/97794 | | 12/2001 |
| WO | WO 02/06280 | | 1/2002 |
| WO | WO 02/14349 | * | 2/2002 |
| WO | WO 02/20475 | | 3/2002 |
| WO | WO 02/50056 | | 6/2002 |
| WO | WO02/062829 | * | 8/2002 |
| WO | WO 02/062829 | * | 8/2002 |
| WO | WO 03/070229 | | 8/2003 |
| WO | WO 2004/062657 | | 7/2004 |

OTHER PUBLICATIONS

Bauer, "Hilfsstoffe," in *Pharmazeutische Technologie.* Sucker et al. (eds.), Georg Thieme Verlag Stuttgart: New York, p. 174-216 (1991).
Bookser et al., "Syntheses of Quadruply Two-and Three-Atom, Aza-Bridged, Cofacial Bis (5,10,15,20-Tetraphenylporphyrins)," *J. Am. Chem. Soc.* 113:4208-4216 (1991).
Cajot et al., "Plasminogen-Activator Inhibitor Type 1 is a Potent Natural Inhibitor of Extracellular Matrix Degradation by Fibrosarcoma and Colon Carcinoma Cells," *Proc. Natl. Acad. Sci. USA* 87:6939-6943 (1990).
Choi-Sledeski et al., "Discovery of an Orally Efficacious Inhibitor of Coagulation Factor Xa Which Incorporates a Neutral $P_1$ Ligand," *J. Med. Chem.* 46:681-684 (2003).
Collen et al., "In Vivo Studies of a Synthetic Inhibitor of Thrombin," *J. Lab. Clin. Med.* 99:76-83 (1982).
Coussens et al., "Matrix Metalloproteinase Inhibitors and Cancer: Trials and Tribulations," *Science* 295:2387-2392 (2002).
Dexter et al., "N,N-Dimethylformamide-induced Alteration of Cell Culture Characteristics and Loss of Tumorigenicity in Cultured Human Colon Carcinoma Cells," *Cancer Res.* 39:1020-1025 (1979).
Dixon, "The Determination of Enzyme Inhibitor Constants," *Biochem. J.* 55:170-171 (1953).
Duggan et al., "Urokinase Plasminogen Activator and Urokinase Plasminogen Activator Receptor in Breast Cancer," *Int. J. Cancer* 61:597-600 (1995).
Enyedy et al., "Structure-Based Approach for the Discovery of Bis-benzamidines as Novel Inhibitors of Matriptase," *J. Med. Chem.* 44:1349-1355 (2001).
Eriksson et al., "The Direct Thrombin Inhibitor Melagatran Followed by Oral Ximelagatran compared with Enoxaparin for the Prevention of Venous Thromboembolism after Total Hip or Knee Replacement: the EXPRESS study," *Journal of Thrombosis and Haemostasis*, 1:2490-2496 (2003).
Fareed, et al., "Inhibition of Serine Proteases by Low Molecular Weight Peptides and Their Derivatives", *Ann. N. Y. Acad. Sci.* 370:765-784 (1981).
Francis et al., "Comparison of Ximelagatran with Warfarin for the Prevention of Venous Thromboembolism after Total Knee Replacement," *N. Engl. J. Med.* 349:1703-1712 (2003).
Frérot et al., "PyBOP® and PyBroP: Two reagents for the difficult coupling of the α,α-dialkyl amino acid, Aib," *Tetrahedron*, 47(2):259-270 (1991).
Friedrich et al., "Catalytic Domain Structures of MT-SP1/Matriptase, a Matrix-degrading Transmembrane Serine Proteinase," *J. Biol. Chem.* 277:2160-2168 (2002).
Garrett et al., "Peptide Aldehyde Inhibitors of the Kallikreins: An Investigation of Subsite Interactions with Tripeptides Containing Structural Variations at the Amino Terminus," *J. Pept. Res.* 52:60-71 (1998).
Griffin, "Role of Surface in Surface-Dependent Activation of Hageman Factor (Blood Coagulation Factor XII)", *Proc. Natl. Acad. Sci. USA* 75:1998-2002 (1978).
Garrett et al., "Synthesis of Potent and Selective Inhibitors of Human Plasma Kallikrein," *Bioorg. Med. Chem. Lett.* 9:301-306 (1999).
Gustafsson et al., "Effects of Melagatran, a New Low-Molecular-Weight Thrombin Inhibitor, on Thrombin and Fibrinolytic Enzymes," *Thromb. Haemost.* 79:110-118 (1998).
Gustafsson et al., "Effects of Inogatran, A New Low-Molecular-Weight Thrombin Inhibitor, in Rat Models of Venous and Arterial Thrombosis, Thrombolysis and Bleeding Time," *Blood Coagulation and Fibrinolysis* 7:69-79 (1996).
Gustafsson et al., "The Direct Thrombin Inhibitor Melagatran and Its Oral Prodrug H 376/95: Intestinal Absorption Properties, Biochemical and Pharmacodynamic Effects," *Thromb. Res.* 101:171-181 (2001).
Gustafsson et al., "A New Oral Anticoagulant: The 50-Year Challenge," *Nature Reviews Drug Discovery* 3:649-659, 2004.
Hara et al., "DX-9065a, a New Synthetic, Potent Anticoagulant and Selective Inhibitor for Factor Xa," *Thromb. Haemost.* 71:314-319 (1994).
Herbert et al., "DX 9065A, a Novel, Synthetic, Selective and Orally Active Inhibitor of Factor Xa: In Vitro and In Vivo Studies," *J. Pharmacol. Exp. Ther.* 276:1030-1038 (1996).
Ho et al., "Exploratory Solid-Phase Synthesis of Factor Xa Inhibitors: Discovery and Application of $P_3$-Heterocyclic Amides as Novel Types of Non-Basic Arginine Surrogates," *Bioorg. Med. Chem. Lett.* 9:3459-3464 (1999).
Hooper et al., "Type II Transmembrane Serine Proteases," *J. Biol. Chem.* 276:857-860 (2001).
Ihara et al., "Prometastatic Effect of N-Acetylglucosaminyltransferase V Is Due to Modification and Stabilization of Active Matriptase by Adding β1-6 GlcNAc Branching," *J. Biol. Chem.* 277:16960-16967 (2002).
Isobe, "Inhibitory Effect of Gabexate (FOY) on Contact System," *Blood & Vessel* 12:135-138 (1981).
Judkins et al., "A Versatile Synthesis of Amidines from Nitriles Via Amidoximes," *Synthetic Communications* 26: 4351-4367 (1996).

(56) References Cited

OTHER PUBLICATIONS

Kang et al., "Tissue Microarray Analysis of Hepatocyte Growth Factor/Met Pathway Components Reveals a Role for Met, Matriptase, and Hepatocyte Growth Factor Activator Inhibitor 1 in the Progression of Node-negative Breast Cancer," *Cancer Res.* 63:1101-1105 (2003).
Kaplan, "Initiation of the Intrinsic Coagulation and Fibrinolytic Pathways of Man: The Role of Surfaces, Hageman Factor, Prekallikrein, High Molecular Weight Kininogen, and Factor XI," *Prog. Hemostasis Thromb.* 4:127-175 (1978).
Kettner et al., "Inactivation of Trypsin-Like Enzymes with Peptides of Arginine Chloromethyl Ketone," *Methods in Enzymology* 80:826-843 (1981).
Kettner et al., "The Selective Inhibition of Thrombin by Peptides of Boroarginine," *J. Biol. Chem.* 265, 18289-18297 (1990).
Kettner et al., "The Selective Affinity Labeling of Factor $X_a$ by Peptides of Arginine Chloromethyl Ketone," *Thromb. Res.* 22:645-652 (1981).
Kim et al., "Preparation of Argatroban Analog Thrombin Inhibitors with Reduced Basic Guanidine Moiety, and Studies of Their Cell Permeability and Antithrombotic Activities," *Med. Chem. Res.* 377-383 (1996).
Kirk, "4-Lithio-1-Tritylimidazole as a Synthetic Intermediate, Synthesis of Imidazole-4-Carboxaldehyde," *J. Heterocyclic Chem.* 22:57-59 (1985).
Kruger et al., "Host TIMP-1 Overexpression Confers Resistance to Experimental Brain Metastasis of a Fibrosarcoma Cell Line," *Oncogene* 16:2419-2423 (1998).
Kruger et al., "The Bacterial *LacZ* Gene: An Important Tool for Metastasis Research and Evaluation of New Cancer Therapies," *Cancer and Metastasis Reviews* 17:285-294 (1999).
Künzel et al., "4-Amidinobenzylamine-Based Inhibitors of Urokinase," *Bioorg. Med. Chem. Lett.* 12:645-648 (2002).
Lawson et al., "Studies on the Inhibition of Human Thrombin: Effects of Plasma and Plasma Constituents Folia Haematol," *Leipzig* 109, 52-60 (1982).
Leadley, "Coagulation Factor Xa Inhibition: Biological Background and Rationale," *Curr. Topics in Med. Chem.*, 1: 151-159 (2001).
Lee et al., "Noncovalent Tripeptidic Thrombin Inhibitors Incorporating Amidrazone, Amine and Amidine Functions at P1," *Bioorg. Med. Chem. Lett.* 12:1017-1022 (2002).
Lee et al., "Noncovalent Thrombin Inhibitors Incorporating an Imidazolylethynyl P1," *Bioorganic & Medicinal Chemistry Letters*, 10:2775-2778 (2000).
Lee et al., "Activation of Hepatocyte Growth Factor and Urokinase/Plasminogen Activator by Matriptase, an Epithelial Membrane Serine Protease," *J. Biol. Chem.* 275:36720-36725 (2000).
Lin et al., "Characterization of a Novel, Membrane-bound, 80-kDa Matrix-degrading Protease from Human Breast Cancer Cells," *J. Biol. Chem.* 272:9147-9152 (1997).
Lin et al., "Molecular Cloning of cDNA for Matriptase, a Matrix-degrading Serine Protease with Trypsin-like Activity," *J. Biol. Chem.* 274:18231-18236 (1999).
Lin et al., "Purification and Characterization of a Complex Containing Matriptase and a Kunitz-type Serine Protease Inhibitor from Human Milk," *J. Biol. Chem.* 274:18237-18242 (1999).
Long et al., "Synthesis and Evaluation of the Sunflower Derived Trypsin Inhibitor as a Potent Inhibitor of the Type II Transmembrane Serine Protease, Matriptase," *Bioorg. Med. Chem. Lett.* 11:2515-2519 (2001).
Maduskuie el al., "Rational Design and Synthesis of Novel, Potent Bis-Phenylamidine Carboxylate Factor Xa Inhibitors," *J. Med. Chem.* 41:53-62 (1998).
Maignan et al., "The Use of 3D Structural Data in the Design of Specific Factor Xa Inhibitors," *Curr. Topics in Med. Chem.* 1:161-174 (2001).
Mignatti et al., "Biology and Biochemistry of Proteinases in Tumor Invasion," *Physiological Reviews* 73:161-195 (1993).
Mohan et al., "Solid-Phase Synthesis of N-Substituted Amidinophenoxy Pyridines as Factor Xa Inhibitors," *Bioorg. Med. Chem. Lett.* 8:1877-1882 (1998).
Morrissette et al., "Low Molecular Weight Thrombin Inhibitors With Excellent Potency, Metabolic Stability, and Oral Bioavailability," *Bioorganic & Med. Chem. Letters*, 14:4161-4164 (2004).
Muramatu et al., "Inhibitory Effects of ω-Amino Acid Esters on Trypsin, Plasmin, Plasma Kallikrein and Thrombin," *Biochim. Biophys. Acta* 242:203-208 (1971).
Muramatu et al., "Inhibitory Effects of ω-Guanidino Acid Esters on Trypsin, Plasmin, Plasma Kallikrein and Thrombin," *Biochim. Biophys. Acta* 268:221-224 (1972).
Muramatu et al., "Inhibitory Effects of Aryl trans-4 (Aminomethyl) Cyclohexanecarboxylate on Serine Proteases, and their Antiallergic Effects," *Hoppe-Seyler's Z. Physiol. Chem.* 363:203-211 (1982).
Nar et al., "Structural Basis for Inhibition Promiscuity of Dual Specific Thrombin and Factor Xa Blood Coagulation Inhibitors," *Structure*, 9:29-37 (2001).
Nelson et al., "Stereoselective Synthesis of a Potent Thrombin Inhibitor by a Novel P2-P3 Lactone Ring Opening," *J. Org. Chem.* 69:3620-3627 (2004).
Oberst et al., "Expression of the Serine Protease Matriptase and Its Inhibitor HAI-1 in Epithelial Ovarian Cancer: Correlation with Clinical Outcome and Tumor Clinicopathological Parameters," *Clin. Cancer Res.* 8:1101-1107 (2002).
Ohno et al., "FOY: [Ethyl-(6-Guanidinohexanoyloxy) Benzoate] Methanesulfonate as a Serine Proteinase Inhibitor. I. Inhibition of Thrombin and Factor Xa in Vitro," *Thromb. Res.* 19:579-588 (1980).
Okada et al., "Development of Plasmin and Plasma Kallikrein Selective Inhibitors and their Effect on M1 (Melanoma) and ht29 Cell Lines," *Bioorg. Med. Chem. Lett.* 10:2217-2221 (2000).
Okada et al., "Development of Plasma Kallikrein Selective Inhibitors," *Biopolymers* 51:41-50 (1999).
Okamoto et al., "Recent Studies of the Synthetic Selective Inhibitors; With Special Reference to Non-Plasmin Fibrinolytic Enzyme, Plasmin and Plasma-Kallikrein Thromb," *Res., Suppl. I*, 131-141 (1988).
Ossowski et al., "Antibodies to Plasminogen Activator Inhibit Human Tumor Metastasis," *Cell* 35:611-619 (1983).
Ostrem et al., "Discovery of a Novel, Potent, and Specific Family of Factor Xa Inhibitors via Combinatorial Chemistry," *Biochemistry* 37:1053-1059 (1998).
Patani et al., "Bioisosterism: A Rational Approach in Drug Design." *Chem. Rev.* 96:3147-3176 (1996), pp. 3147-3148 and 3170.
Pauls et al., "The Design of Competitive, Small-Molecule Inhibitors of Coagulation Factor Xa," *Frontiers in Med. Chem.*, 1:129-152 (2004).
Pedersen et al., "Prognostic Impact of Urokinase, Urokinase Receptor, and Type 1 Plasminogen Activator Inhibitor in Squamous and Large Cell Lung Cancer Tissue" *Cancer Research* 54:4671-4675 (1994).
Perzborn et al., "In Vitro and In Vivo Studies of the Novel Antithrombotic Agent BAY 59-7939—an Oral, direct Factor Xa Inhibitor," *J. Thromb. & Haemost.* 3:514-521 (2005).
Phillips et al., "Discovery of N-[2-[5-[Amino(imino)methyl]-2-hydroxyphenoxy]-3,5-difluoro-6-[3-(4,5-dihydro-1-methyl-1H-imidazol-2-yl)phenoxy]pyridin-4-yl]-N-methylglycine (ZK-807834): A Potent, Selective, and Orally Active Inhibitor of the Blood Coagulation Enzyme Factor Xa," *J. Med. Chem.* 41:3557-3562 (1998).
Quan et al., "Bisbenzamidine Isoxazoline Derivatives as Factor Xa Inhibitors," *Bioorg. Med. Chem. Lett.* 7:2813-2818 (1997).
Quan et al., "Discovery of 1-(3'-Aminobenzisoxazol-5'-yl)-3-trifluormethyl-N-[2-fluoro-4-[(2'-dimethylaminomethyl)imidazol-1-yl]phenyl]-1H-pyrazole-5-carboxyamide Hydrochloride (Razaxaban), a Highly Potent, Selective, and Orally Bioavailable Factor Xa Inhibitor," *J. Med. Chem.* 48:1729-1744 (2005).
Quan et al., "The Race to Orally Active Factor Xa Inhibitor: Recent Advances," *Curr. Opin. In Drug Discovery & Development*, 7:460-469 (2004).
Ratnoff, "Studies on the Inhibition of Ellagic Acid-Activated Hageman factor (factor XII) and Hageman factor fragments," *Blood* 57:55-58 (1981).

(56) References Cited

OTHER PUBLICATIONS

Renatus et al., "Structural and Functional Analyses of Benzamidine-based Inhibitors in Complex with Trypsin: Implications for the Inhibition of Factor Xa, tPA, and Urokinase." *J. Med. Chem.* 41:5445-5456 (1998).
Reuning et al., "Multifunctional Potential of the Plasminogen Activation System in Tumor Invasion and Metastasis (Review)," *International Journal of Oncology* 13:893-906 (1998).
Rittle et al., "Unexpected Enhancement of Thrombin Inhibitor Potency with o-Aminoalkylbenzylamides in the P1 Position," *Bioorg. Med. Chem. Lett.* 13:3477-3482 (2003).
Robinson et al., "Chapter 9. Anticoagulants: Inhibitors of the Factor VIIa/Tissue Factor Pathway," *Ann. Rep. Med. Chem.* 37:85-94 (2002).
Rubini et al., "Synthesis of Isosteric Methylene-oxy Pseudopeptide Analogues as Novel Amide Bond Surrogate Units." *Tetrahedron* 43(21):6039-6045 (1986).
Sato et al., "Antithrombotic Effects of YM-60828, a Newly Synthesized Factor Xa Inhibitor, in Rat Thrombosis Models and Its Effects on Bleeding Time," *Br. J. Pharmacol.* 123:92-96 (1998).
Sato et al., "YM-60828, a Novel Factor Xa Inhibitor: Separation of Its Antithrombotic Effects from Its Prolongation of Bleeding Time," *Eur. J. Pharmacol.* 339:141-146 (1997).
Satoh et al., "Medicinal Chemical Studies on Synthetic Protease Inhibitors, trans-4-Guanidinomethylcyclohexanecarboxylic Acid Aryl Esters," *Chem. Pharm. Bull.* 33:647-654 (1985).
Schechter et al., "On the Size of the Active Site in Proteases. I. Papain," *Biochem. Biophys. Res. Commun.* 27:157-162 (1967).
Schmitt et al., "Clinical Impact of the Plasminogen Activation System in Tumor Invasion and Metastasis: Prognostic Relevance and Target for Therapy," *Thrombosis and Haemostasis* 78:285-296 (1997).
Shi et al., "Identification and Characterization of a Novel Matrix-degrading Protease from Hormone-dependent Human Breast Cancer Cells," *Cancer Res.* 53:1409-1415 (1993).
Silverberg et al., "Enzymatic activities of activated and zymogen forms of human Hageman factor (factor XII)," *Blood* 60:64-70 (1982).
Soll et al., "Amidinohydrazones as Guanidine Bioisosteres: Application to a New Class of Potent, Selective and Orally Bioavailable, Non-Amide-Based Small Molecule Thrombin Inhibitors," *Bioorganic & Medicinal Chemistry Letters* 10:1-4 (2000).
Sperl et al., "(4-Aminomethyl) Phenylguanidine Derivates as Nonpeptidic Highly Selective Inhibitors of Human Urokinase," *Proc. Natl. Acad. Sci. USA* 97:5113-5118 (2000).
Sperl et al., "Urethanyl-3-Amidinophenylalanine Derivatives as Inhibitors of Factor Xa. X-Ray Crystal Structure of a Trypsin/Inhibitor Complex and Modeling Studies," *Biol. Chem.* 381:321-329 (2000).
Stauffer et al., "9-Hydroxyazafluorenes and their Use in Thrombin Inhibitors," *J. Med. Chem.*, 48: 2282-2293 (2005).
Stephens et al., "The Urokinase Plasminogen Activator System as a Target for Prognostic Studies in Breast Cancer," *Breast Cancer Research and Treatment*, 52:99-111 (1998).
Stürzebecher et al., "Novel Plasma Kallikrein Inhibitors of the Benzamidine Type," *Brazilian Journal Med. Biol. Res.* 27:1929-1934 (1994).
Stürzebecher et al., "3-Amidinophenylalanine-Based Inhibitors of Urokinase," *Bioorganic & Medicinal Chemistry Letters* 9:3147-3152 (1999).
Stürzebecher et al., "Synthesis and Structure-Activity Relationships of Potent Thrombin Inhibitors: Piperazides of 3-Amidinophenylalanine," *J. Med. Chem.* 40:3091-3099 (1997).
Stürzebecher et al., "Synthetic Inhibitors of Bovine Factor Xa and Thrombin Comparison of Their Anticoagulant Efficiency," *Thromb. Res.* 54:245-252 (1989).
Stürzebecher et al., *Zentralbl. Pharm. Pharmakother. Lab. Diagn.* 122:240-241 (1983).
Sucker et al., *Pharm. Techn. 2.*, Bauer, Georg Thieme Verlag, Stuttgart, (1991).

Tada et al., "Isolation of Plasma Kallikrein by High Efficiency Affinity Chromatography and Its Characterization," *Biol. Pharm. Bull.* 24:520-524 (2001).
Takeuchi et al., "Reverse Biochemistry: Use of Macromolecular Protease Inhibitors to Dissect Complex Biological Processes and Identify a Membrane-type Serine Protease in Epithelial Cancer and Normal Tissue," *Proc. Natl. Acad. Sci. USA* 96:11054-11061 (1999).
Takeuchi et al., "Cellular Localization of Membrane-type Serine Protease 1 and Identification of Protease-activated Receptor-2 and Single-chain Urokinase-type Plasminogen Activator as Substrates," *J. Biol. Chem.* 275:26333-26342 (2000).
Tamura et al., "Synthesis and Biological Activity of Peptidyl Aldehyde Urokinase Inhibitors." *Bioorganic & Medicinal Chemistry Letters*, 10:983-987 (2000).
Teno et al., "Development of Selective Inhibitors against Plasma," Kallikrein *Chem. Pharm. Bull.* 39:2930-2936 (1991).
Towle et al., "Inhibition of Urokinase by 4-Substituted Benzo[b]thiophene-2-Carboxamidines: An Important New Class of Selective Synthetic Urokinase Inhibitor," *Cancer Research* 53:2553-2559 (1993).
Tucker et al., "Potent Noncovalent Thrombin Inhibitors That Utilize the Unique Amino Acid d-Dicyclohexylalanine in the P3 Position. Implications on Oral Bioavailability and Antithrombotic Efficacy," *J. Med. Chem.* 40:1565-1569 (1997).
Tucker et al., "Synthesis of a Series of Potent and Orally Bioavailable Thrombin Inhibitors That Utilize 3,3-Disubstituted Propionic Acid Derivatives in the P3 Position," *J. Med. Chem.* 40:3687-3693 (1997).
Tsuda et al., Structure-Inhibitory Activity Relationship of Plasmin and Plasma Kallikrein Inhibitors, *Chem. Pharm. Bull.* 49:1457-1463 (2001).
Vassalli et al., "Amiloride Selectively Inhibits the Urokinase-Type Plasminogen Activator," *FEB* 214:187-191 (1987).
von der Saal et al, "Derivatives of 4-Amino-Pyridine as Selective Thrombin Inhibitors," *Bioorganic & Medicinal Chemistry Letters* 7:1283-1288 (1997).
Wagner et al., "Synthese von N-[Amidinobenzyl]-und N-[Amidinophenyl]-Phthalimide und-1-Oxoisoindoline," *Pharmazie* 32:76-79 (1977).
Weitz, "New Anticoagulants for Treatment of Venous Thromboembolism," *Circulation*, 110:I-19-I-26 (2004).
Wikström et al., "Development and Validation of a Chiral Capillary Electrophoresis Method for Melagatran and Ximelagatran Drug Substances," *J. Sep. Sci.* 25:1167-1174 (2002).
Zeslawska et al., "Crystals of the Urokinase Type Plasminogen Activator Variant βc-uPA in Complex with Small Molecule Inhibitors Open the Way towards Structure-based Drug Design," *J. Mol. Biol.* 301:465-475 (2000).
Zeslawska et al., "Crystals of Urokinase Type Plasminogen Activator Complexes Reveal the Binding Mode of Peptidomimetic Inhibitors," *J. Mol.Biol.* 328:109-118 (2003).
Zhang et al., "Assignment of Human Putative Tumor Suppressor Genes ST13 (alias SNC6) and ST14 (alias SNC19) to Human Chromosome Bands 22q13 and 11q24→q25 by In Situ Hybridization," *Cytogenet. Cell Genet.* 83:56-57 (1998).
Zhu et al., "Recent Advances in Inhibitors of Factor Xa in the Prothrombinase Complex," *Curr. Opin. Cardiovasc. Pulmon. Renal Invest. Drugs* 1:63-87 (1999).
Office Action pertaining to U.S. Appl. No. 10/297,557 mailed Nov. 4, 2003.
Office Action pertaining to U.S. Appl. No. 10/311,364 mailed Nov. 19, 2003.
Office Action pertaining to U.S. Appl. No. 10/311,364 mailed Apr. 1, 2004.
Office Action pertaining to U.S. Appl. No. 10/506,579 mailed Dec. 16, 2009.
Office Action pertaining to U.S. Appl. No. 10/506,579 mailed Jan. 30, 2009.
Office Action pertaining to U.S. Appl. No. 10/506,579 mailed Jul. 17, 2008.
Office Action pertaining to U.S. Appl. No. 10/555,821, mailed Jan. 21, 2009.
Office Action pertaining to U.S. Appl. No. 10/571,026, mailed Dec. 13, 2007.

(56) References Cited

OTHER PUBLICATIONS

Office Action pertaining to U.S. Appl. No. 10/571,026, mailed Feb. 23, 2009.
Office Action pertaining to U.S. Appl. No. 10/571,026, mailed Oct. 30, 2009.
International Search Report for International Application No. PCT/EP2004/000247, dated Aug. 18, 2004.
International Preliminary Report on Patentability for International Application No. PCT/EP2004/000247, dated Sep. 2, 2005.
Written Opinion of the International Search Authority for International Application No. PCT/EP2004/000247, dated Aug. 18, 2004.
Banke et al., "Increase of Anti-Metastatic Efficacy by Selectivity- But Not Affinity-Optimization of Synthetic Serine Protease Inhibitors," *Biol. Chem.* 384: 1515-1525 (2003).
Clement, "Reduction of N-Hydroxylated Compounds: Amidoximes (N-Hydroxyamidines) As Pro-Drugs of Amidines," *Drug Metabolism Reviews*, 34(3)(1)565-579 (2002).
Extended European Search Report pertaining to European Patent Application No. 10013065.7-2123.

\* cited by examiner

ACYLATED 4-AMIDINO- AND -4-GUANIDINOBENZYLAMINES FOR INHIBITION OF PLASMA KALLIKREIN

CROSS REFERENCE TO RELATED APPLICATIONS

This application is the U.S. National Stage of International Application No. PCT/EP2004/000247, filed Jan. 15, 2004, which claims benefit of German Application No. 10301300.8, filed Jan. 15, 2003, hereby incorporated by reference.

The invention relates to the use of acylated 4-amidinobenzylamine or 4-guanidinobenzylamine in accordance with the general formula P4-P3-P2-P1 (I), with P4 being a monosubstituted or polysubstituted or unsubstituted benzylsulfonyl group, P3 being a monosubstituted or polysubstituted or unsubstituted, natural or unnatural, α-amino acid or α-imino acid in the D configuration, P2 being a monosubstituted or polysubstituted or unsubstituted, natural or unnatural, α-amino acid or α-imino acid in the L configuration, and P1 being a monosubstituted or polysubstituted or unsubstituted 4-amidino- or 4-guanidinobenzylamine group, for inhibiting plasma kallikrein (PK). In this connection, the novel PK inhibitors are employed for prevention of the activation of coagulation at synthetic surfaces and for systemic administration as anticoagulants/antithrombotic agents, especially for prevention of the activation of coagulation at synthetic surfaces, in order to prevent thromboembolic events.

The present invention furthermore relates to the novel acylated 4-amidino- or 4-guanidinobenzylamines per se, with preference being given, in particular, to those which possess a linker group at P2 or P4, with these linker groups preferably being, in particular, oligo- or polyalkylene glycols.

The present invention also relates to the use of the abovementioned acylated 4-amidino- or 4-guanidinobenzylamines for inhibiting factor XIa and/or factor XIIa. The use of the abovementioned compound for inhibiting thrombin and prothrombin is also described within the context of the present invention.

PK is a multifunctional, trypsin-like serine protease for which several physiological substrates are known. Thus, PK can, by means of proteolytic cleavage, liberate the vasoactive peptide bradykinin from high molecular weight kininogen and activate the proteases coagulation factor XII, prourokinase, plasminogen and Pro-MMP 3. It is therefore assumed that the PK/kinin system plays an important role in a variety of syndromes, for example in thromboembolic situations, disseminated intravasal coagulation, septic shock, allergies, the postgastrectomy syndrome, arthritis and ARDS (adult respiratory distress syndrome) (Tada et al., Biol. Pharm. Bull 24, 520-524, 2001).

As a result of activating coagulation factor XII, thus transforming it into factor XIIa, PK plays an especial role in the activation of the intrinsic coagulation cascade. The intrinsic coagulation cascade can become activated if blood which is present in extracorporeal blood circulations comes into contact with synthetic surfaces, for example in connection with hemodialysis or in connection with using oxygenators. As a result of factor XII being bound to, in particular, negatively charged surfaces and/or synthetic surfaces, the intrinsic coagulation cascade is triggered by means of autoactivation or by traces of PK (Kaplan, Prog. Hemostasis Thromb. 4, 127-175, 1978). The activated factor XII (F XIIa) catalyzes the conversion of plasma prekallikrein to PK, which, in the sense of a positive feedback, brings about further formation of factor XIIa (Griffin, Proc. natl. Acad. Sci. USA 75, 1998-2002, 1978). In conformity with the significance of factor XIIa and PK in the early phase of the intrinsic coagulation cascade, inhibitors of these enzymes should also have a coagulation-inhibiting effect. During this early phase in the activation of intrinsic coagulation, factor XIIa activates factor XI thereby converting the latter into factor XIa.

Anticoagulants of the heparin type, vitamin K antagonists or hirudin are used as inhibitors of both the intrinsic and the extrinsic coagulation cascades and thus for the prophylaxis and therapy of the abovementioned syndromes, such as thromboembolic situations, disseminated intravasal coagulation, septic shock, allergies, the postgastrectomy syndrome, arthritis and ARDS. Since, however, the current anticoagulants do not meet all the requirements placed on an "ideal" antithrombotic agent, for example because of their low specificity, because of bleeding complications which arise, because of a low half-life or because of inadequate oral availability, attempts are being made to use small-molecule inhibitors of the coagulation proteases thrombin and factor Xa to develop alternatives. Factor VIIa, which is the initial enzyme in the extrinsic coagulation pathway, is another target enzyme which is being investigated in a variety of ways for the purpose of developing inhibitors (Robinson and Saiah, Ann. Rep. Med. Chem. 37, 85-94, 2002). However, an inhibitor of thrombin and F Xa, or an inhibitor of F VIIa as a specific inhibitor of the extrinsic coagulation cascade, does not have any inhibitory effect on the activation of the intrinsic coagulation cascade which is induced, for example, by contact of the blood with synthetic surfaces.

There are only a few approaches with regard to searching for inhibitors for the two enzymes factor XIIa and PK, which institute intrinsic coagulation following activation at a charged surface. The guanidinoalkylcarboxylic acid derivative FOY (Isobe, Blood & Vessel 12, 135-138, 1981), leupeptin, the thrombin inhibitor Nα-dansyl-L-arginine-4-ethylpiperidide (Ratnoff, Blood 57, 55-58, 1981) and a variety of tripeptides (esters and amides) (Fareed et al. Ann. N. York Acad. Sci. 370, 765-784, 1981; Silverberg and Kaplan, Blood 60, 64-70, 1982) have been reported to have some degree of inhibitory effect on factor XIIa. Amides of Nα-substituted 4-amidinophenyl-α-aminobutyric acid have been reported to be more active inhibitors (Stürzebecher et al., Zentralbl. Pharm. Pharmakother. Lab. Diagn. 122, 240-241, 1983).

A variety of bisbenzamidines such as pentamidine and related compounds having $K_i$ values around 50 μM have been found to be active PK inhibitors (Ashgar et al., Biochim. Biophys. Acta 438, 250-264, 1976). Esters of ω-amino- and ω-guanidinoalkylcarboxylic acids have also been reported to be PK inhibitors having micromolar $K_i$ values (Maramatu and Fuji, Biochim. Biophys. Acta 242, 203-208, 1971; Muramatu and Fuji, Biochim. Biophys. Acta 268, 221-224, 1972; Ohno et al. Thromb. Res. 19, 579-588, 1980; Muramatu et al. Hoppe-Seyler's Z. Physiol. Chem. 363, 203-211, 1982; Satoh et al. Chem. Pharm. Bull. 33, 647-654, 1985; Teno et al. Chem. Pharm. Bull. 39, 2930-2936, 1991). The first highly selective competitive inhibitors, which are derived from arginine or phenylalanine, were developed by Okamoto et al. (Thromb. Res., Suppl. VIII, 131-141, 1988) and inhibit PK with $K_i$ values around 1 μM. Okada's group has published several studies on the development of competitive PK inhibitors, with the most active compounds, which are derived from trans-4-aminomethylcyclohexanecarbonyl-Phe-4-carboxymethylanilide, having inhibitory constants around 0.5 μM (Okada et al., Biopolymers 51, 41-50, 1999; Okada et al., Bioorg. Med. Chem. Lett. 10, 2217-2221; 2000, Tsuda et al., Chem. Pharm. Bull. 49, 1457-1463, 2001). A feature possessed in common by the abovementioned PK inhibitors is their relatively high $K_i$ value. WO 00/41531 described potent PK inhibitors which have inhibitory constants around 1 nM and which possess a 4-amidinoaniline as the P1 radical. However, these inhibitors described in WO 00/41531 are not suitable for being coupled covalently to synthetic surfaces. PK inhibitors have also been described in WO 94/29336. The essential difference as compared with the compounds in accordance with the present invention is that the compounds described in WO 94/29336 do not contain the crucial benzylsulfonyl radical (P4). Furthermore, WO 94/29336 did not describe any coupling of the compounds to, for example, synthetic surfaces.

By now, some transition state-analogous PK inhibitors, which possess an arginal (e.g. adamantyloxycarbonyl-D-Phe-Phe-arginal, $K_i$ 12 nM, Garrett et al., J. Pept. Res. 52, 60-71, 1998) or arginyl trifluoromethyl ketone (e.g. adamantyloxycarbonyl-D-tert-butylglycine-Phe-Arg-CF$_3$, $K_i$ 2 nM, Garrett et al., Bioorg. Med. Chem. Lett. 9, 301-306, 1999) as the P1 radical, have also been described. The boroarginine derivative DuP 714 (Ac-D-Phe-Pro-boroarginine), which was originally developed as a thrombin inhibitor, has also been found to be a powerful inhibitor of PK ($K_i$ 1.6 nM) (Kettner et al., J. Biol. Chem. 265, 18289-18297). However, these transition state-analogous protease inhibitors suffer from the disadvantage that they can only be obtained by means of elaborate syntheses and tend to racemize, and are very nonspecific inhibitors.

PK is also inhibited irreversibly by a variety of chloromethyl ketones. H-Ala-Phe-ArgCH$_2$Cl and H-Pro-Phe-ArgCH$_2$Cl have been reported to be the most reactive compounds (Kettner and Shaw, Biochemistry 17, 4778-4784, 1978). However, peptidyl chloromethyl ketones are only suitable for research purposes since, in vivo, they are only stable for a few minutes (Lawson et al., Folia Haematol. (Leipzig) 109, 52-60, 1982; Collen et al., J. Lab. Clin. Med. 99, 76-83, 1982).

The invention is therefore based on the object of providing active compounds which are suitable for therapeutic applications, which inhibit plasma kallikrein with a high degree of activity and specificity and which, following coupling to a synthetic surface or following parenteral, enteral or topical administration, in particular intravenous or subcutaneous administration, have a coagulation-inhibiting effect.

It has been found, surprisingly, that acylated 4-amidino- or 4-guanidinobenzylamine in accordance with the general formula P4-P3-P2-P1 (I), with P4 (following the definition in accordance with Schechter and Berger, Biochem. Biophys. Res. Comm. 27, 157-162) being a monosubstituted or polysubstituted or unsubstituted benzylsulfonyl group, P3 being monosubstituted or polysubstituted or unsubstituted, natural or unnatural, α-amino acid or α-imino acid in the D configuration, P2 being a monosubstituted or polysubstituted or unsubstituted, natural or unnatural, α-amino acid or α-imino acid in the L configuration, and P1 being a monosubstituted or polysubstituted or unsubstituted 4-amidino- or 4-guanidinobenzylamine group, inactivates plasma kallikrein very effectively, has a coagulation-inhibiting effect even after being coupled to a synthetic surface and can be used either parenterally, enterally or topically, in particular intravenously or subcutaneously.

A particular advantage of the acylated 4-amidino- or 4-guanidinobenzylamine derivatives according to the invention is consequently their ability to inactivate PK with high activity even after binding to a synthetic surface. The compounds according to the invention therefore constitute a novel group of highly active and, in particular, couplable plasma kallikrein inhibitors.

Within the meaning of the present invention, a synthetic surface is a surface which is composed, for example, of cellulose diacetate, cellulose triacetate, poly(ether sulfone), poly (aryl ether sulfone), regenerated cellulose, cuprophan, hemophan, poly(sulfone), poly(acrylonitrile), poly(vinyl alcohol), poly(carbonate), poly(amide), poly(methyl methacrylate), poly(ethylene-co-vinyl alcohol) or another material which is used in appliances such as dialyzers, oxygenators, catheters and membranes, and/or the hose systems and air traps which belong to the appliances, which come into contact with blood, particularly in extracorporeal circulations, with the surface materials being modified, where appropriate, with functional groups, e.g. amino groups, aminoalkyl groups, carboxyl groups, carboxyalkyl groups, mercapto groups, mercaptoalkyl groups, hydroxyl groups or hydroxyalkyl groups in order to permit covalent coupling of the inhibitors.

According to a preferred embodiment, the substituent at the substituted P4, P3, P2 and/or P1 is hydrogen and/or a halogen, preferably fluorine, chlorine and/or bromine, and/or a substituted or unsubstituted, branched or linear alkyl radical having 1-6 C atoms, preferably 1-3 C atoms, in particular methyl, or a substituted or unsubstituted, branched or linear aralkyl radical having 1-10 C atoms, with the substituent of the substituted, branched or linear alkyl radical or aralkyl radical preferably being a halogen, hydroxyl, amino, cyano, amidino, guanidino and/or carboxyl group, where appropriate esterified with a lower alkyl radical, in particular with methyl or ethyl, and/or being a hydroxyl, amino, cyano, amidino, guanidino, methyloxycarbonyl, benzyl, benzyloxycarbonyl, aminomethyl or glutaryl or succinylamidomethyl group, and/or being an oxyalkylcarbonyl, carboxyl, carboxymethyl or carboxyethyl group, where appropriate esterified with a lower alkyl radical, in particular with methyl or ethyl, or an oxyalkylcarbonyl, carboxyl, carboxymethyl or carboxyethyl group which is present as unsubstituted amide or amide which is substituted by an alkyl or aryl group.

Unless otherwise stated, an alkyl radical within the meaning of the present invention is always to be understood as being an alkyl radical having 1-12 C atoms, while an aryl radical is always to be understood as being an aryl radical having 6-10 C atoms and an aralkyl radical is always to be understood as being an aralkyl radical having 6 to 12 C atoms.

Within the meaning of the present invention, a lower alkyl radical is understood as being an alkyl radical having 1 to 6 C atoms, preferably 1-3 C atoms.

A linker group can additionally be coupled to P4 or P2, with the linker group being coupled to P4 by way of one of the above-described substituents or coupled directly to a functional group of P2, in particular by way of a —NH— or —CO— group.

A linker group within the meaning of the present invention is defined as being a chemical structure which exhibits at least one functional group for covalent coupling to an acylated 4-amidino- or 4-guanidinobenzylamine by way of P4 or P2 and, in addition, exhibits either at least one second functional group for simultaneous covalent coupling to a synthetic surface or for the simultaneous coupling of a second molecule of the acylated 4-amidino- or 4-guanidinobenzylamine and/or exhibits an oligo- or polyalkylene glycol group which is able to couple noncovalently to the synthetic surface by interacting with it.

A linker group according to the present invention is therefore preferably a dicarboxylic acid, an aminocarboxylic acid, a diamine, a disulfonic acid or an aminosulfonic acid having an alkyl, aryl or aralkyl skeletal structure, with the alkyl skeletal structure exhibiting from 1 to 12 C atoms, in particular 2-6 C atoms, the aryl skeletal structure exhibiting 6-10 C atoms, in particular phenyl, and the aralkyl skeletal structure exhibiting 6-12 C atoms, in particular benzyl, or an aminoalkyl or carboxyalkyl group having 2-12 C atoms, in particular 2-6 C atoms; or with the linker group at P4 or P2 being an oligo- or polyalkylene glycol chain, in particular being a poly- or oligoethylene or poly- or oligopropylene glycol chain, with the oligo- or polyalkylene glycol exhibiting a functional group, in particular a substituted or unsubstituted amino, carboxyl and/or mercapto group, at least at both ends, or with the oligo- or polyalkylene glycol exhibiting a functional group, in particular a substituted or unsubstituted amino, carboxyl and/or mercapto group, at least at one end, and being modified with a $CH_3$ group at the other end.

When the linker group is coupled to P4, the linker group is preferably coupled to P4 by way of a —NH— group, —NH-alkyl group having from 1 to 6 C atoms, in particular methyl, a —CO— group, a —CO-alkyl group having 2-6 C atoms, in particular —CO-methyl, a —CO—O-alkyl group having 1-6 C atoms, in particular methyl, a —S— group, a —S-alkyl group having from 1 to 6 C atoms, in particular methyl, a —O-alkyl group having 1-6 C atoms, in particular methyl, a —$SO_2$— group or a —$SO_2$-alkyl group having 1-6 C atoms, in particular methyl.

Instead of being coupled to P4, the linker group can also be coupled to P2, with P2 preferably being lysine or its homologs having 1-5 C atoms in the side chain, in particular ornithine, homolysine, α,γ-diaminobutyric acid, α,β-diaminopropionic acid, α-diaminoglycine or glutamic acid or its homologs having 1-5 C atoms in the side chain, in particular aspartic acid, glutamic acid or homoglutamic acid or cysteine or homocysteine or serine or threonine.

According to a preferred embodiment of the present invention, the linker group which is coupled to P4 exhibits, together with the substituent for the coupling to P4, the general formula U—Z—Y—X— (II), where U is an $H_2N$—, HOOC—$(CH_2)$—CO—NH—, HOOC—, $H_2N$—$(CH_2)_n$—NH—CO— or HS-group, with Z being —$(CH_2)_n$—, in which n=1 to 10, in particular 1-5, or Z being an oligo- or polyalkylene glycol of the general formula —$(CH_2)_d$—[O—$CH_2$—$CH_2$]$_v$O—$(CH_2)_m$—(NH—CO—$CH_2$—O—$CH_2$)$_k$— or —$(CH_2)_d$—[O—$CH(CH_3)$—$CH_2$]$_v$—O— $(CH_2)_m$—(NH—CO—$CH_2$—O—$CH_2$)$_k$— in which d=1, 2, 3 or 4, v=an integer of from 1 to 1000, preferably of from 1 to 50, in particular of from 2 to 10, m=0, 1, 2, 3 or 4 and k=0 or 1 or U is a $CH_3$—O-group with Z being an oligo- or polyalkylene glycol of the general formula —$(CH_2)_d$—[O—$CH_2$—$CH_2$]$_v$O—$(CH_2)_m$—(NH—CO—$CH_2$—O—$CH_2$)$_k$— or —$(CH_2)_d$—[O—$CH(CH_3)$—$CH_2$]$_v$—O—$(CH_2)_n$—(NH—CO—$CH_2$—O—$CH_2$)$_k$— in which d=1, 2, 3 or 4, v=an integer of from 1 to 1000, preferably of from 1 to 50, in particular of from 2 to 10, m=0, 1, 2, 3 or 4 and k=0 or 1; Y is a —CO—NH— group, a —NH—CO— group, a —$SO_2$—NH— group, a —NH—$SO_2$— group, a —S—S— group or a —S— group, or, if U and Z are not present, is a $H_2N$— group, HOOC— group, HS— group, HO— group or halogenoalkyl group; X is a —$(CH_2)_n$— group in which n=0, 1, 2, 3 or 4, in particular n=1, or is a —$(CH_2)_n$—O— group having a bond to the benzyl radical by way of the oxygen and n=1, 2, 3 or 4. The coupling of the linker group to the benzyl radical is from X, if present, or from Y, if X is not present.

If the linker is coupled to P4, P2 is then glycine, alanine, proline, homoproline or azetidinecarboxylic acid.

According to another preferred embodiment, the linker group is coupled to P2, with P2 exhibiting the general formula III

where q=0, 1, 2, 3, 4 or 5 and D is the formula

where U, Z and Y have the same meaning as in formula II.

According to a particularly preferred embodiment, the acylated amidino- or guanidinobenzylamine exhibits the general formula V or VI

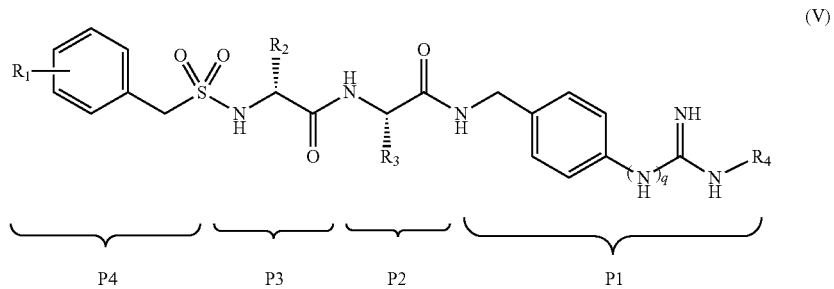

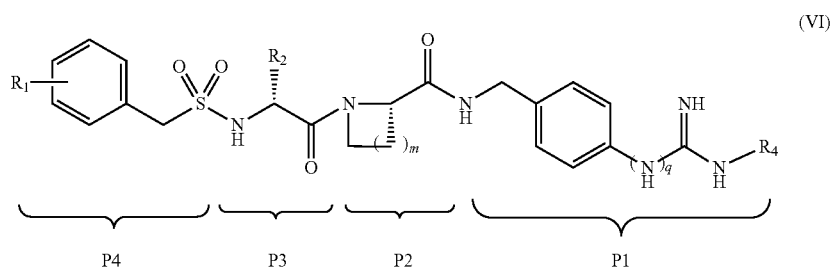

where m=1 to 3 and q is 0 or 1, in particular 0, and where $R_1$, $R_2$, $R_3$ and/or $R_4$ is hydrogen and/or a halogen, preferably fluorine, chlorine and/or bromine, and/or a substituted or unsubstituted, branched or linear alkyl radical having 1-6 C atoms, preferably 1-3 C atoms, in particular methyl, with the substituent of the substituted, branched or linear alkyl radical preferably being a halogen, hydroxyl, amino, cyano, amidino, guanidino and/or carboxyl group, where appropriate esterified with a lower alkyl radical, in particular with methyl or ethyl, and/or being a hydroxyl, amino, cyano, amidino, guanidino, methyloxycarbonyl, benzyl, benzyloxycarbonyl, aminomethyl or glutaryl or succinylamidomethyl group and/or being an oxyalkylcarbonyl, carboxyl, carboxymethyl or carboxyethyl group, where appropriate esterified with a lower alkyl radical, in particular with methyl or ethyl, or being present as unsubstituted amide or amide which is substituted by an alkyl or aryl group.

Within the context of the present invention, the hydroxyl radical, an amino radical and an alkoxycarbonyl radical, in particular an alkoxycarbonyl radical having from 2 to 10 C atoms, are particularly preferred as radicals $R_4$.

$R_1$ and/or $R_3$ can additionally be a linker group, where the linker group is coupled to P4 by way of one of the above-described substituents or coupled directly to a functional group of P2, in particular by way of a —NH— or a —CO— group, with the linker group preferably being a dicarboxylic acid, an aminocarboxylic acid, a diamine, a disulfonic acid or an aminosulfonic acid having an alkyl, aryl or aralkyl skeletal structure, with the alkyl skeletal structure exhibiting from 1 to 12 C atoms, in particular 2-6 C atoms, the aryl skeletal structure exhibiting 6-10 C atoms, in particular phenyl, and the aralkyl skeletal structure exhibiting 6-12 C atoms, in particular benzyl, or an aminoalkyl or carboxyalkyl group having 2-12 C atoms, in particular 2-6 C atoms; or with the linker group at P4 or P2 being an oligo- or polyalkylene glycol chain, in particular a poly- or oligoethylene or poly- or oligopropylene glycol chain, with the oligo- or polyalkylene glycol exhibiting a functional group, in particular a substituted or unsubstituted amino, carboxyl and/or mercapto group, at least at both ends, or with the oligo- or polyalkylene glycol exhibiting a functional group, in particular a substituted or unsubstituted amino, carboxyl and/or mercapto group, at least at one end and being modified with an alkyl group having 1-4 C atoms, in particular $CH_3$ group, at the other end, and/or $R_1$ additionally exhibiting the formula (II) as defined above and P2 together with $R_3$ additionally exhibiting the formulae (III) and (IV) as defined above.

Preferred exemplary embodiments of acylated amidino- and/or guanidinobenzylamines in accordance with the general formula I having a linker group at P4 in accordance with the general formula II preferably exhibit one of the following structures:

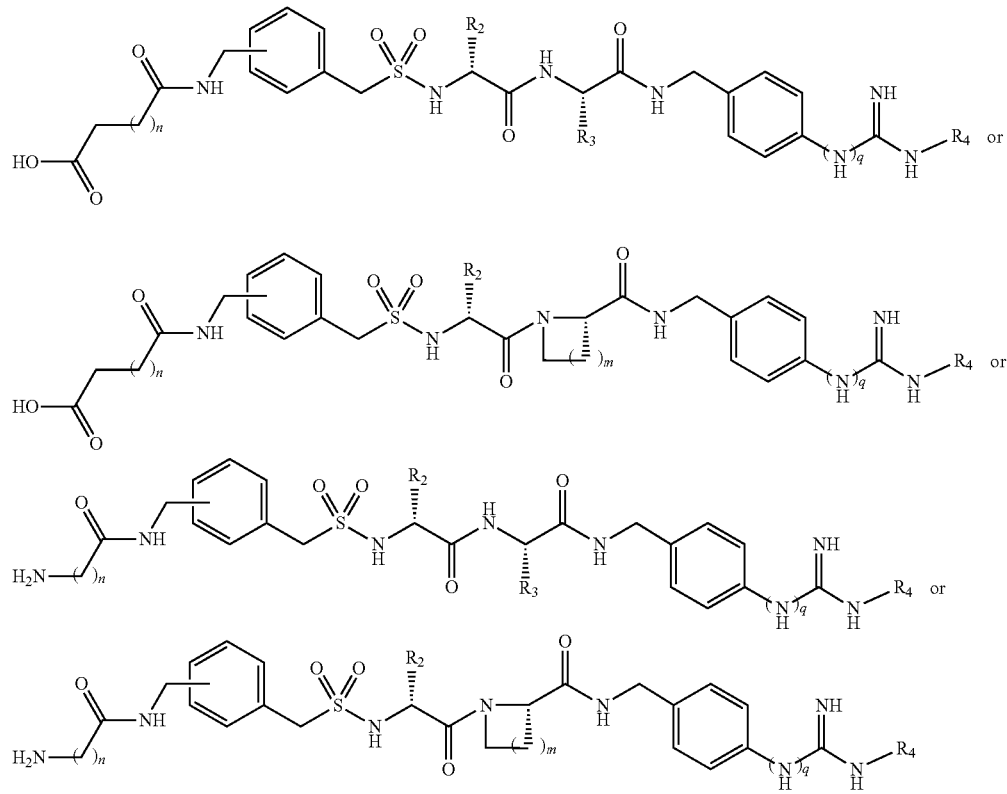

in which n=1 to 10, m=1 to 3 and q=0 or 1, in particular 0, where $R_2$ and $R_3$ have the abovementioned meanings. By means of the presence of a second functional group, such as $H_2N$— or HOOC—, the above-listed substances can be coupled covalently to synthetic surfaces concomitantly with the coupling to P4.

Other preferred exemplary embodiments of acylated amidino- and/or guanidinobenzylamines in accordance with the general formula I having a linker group at P4 in accordance with the general formula II preferably exhibit the following structures:
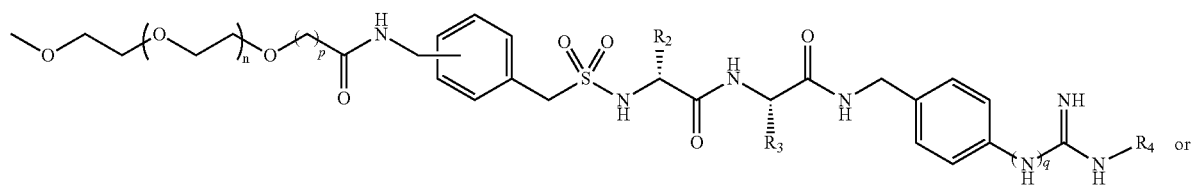
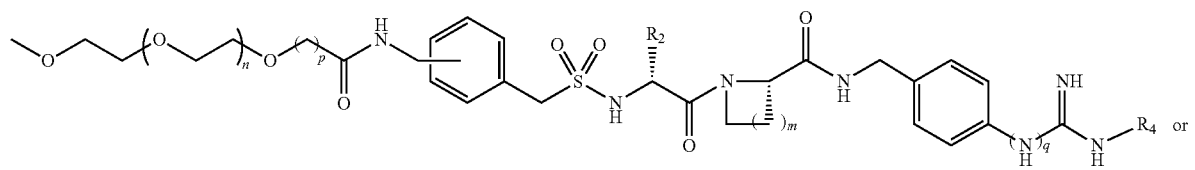
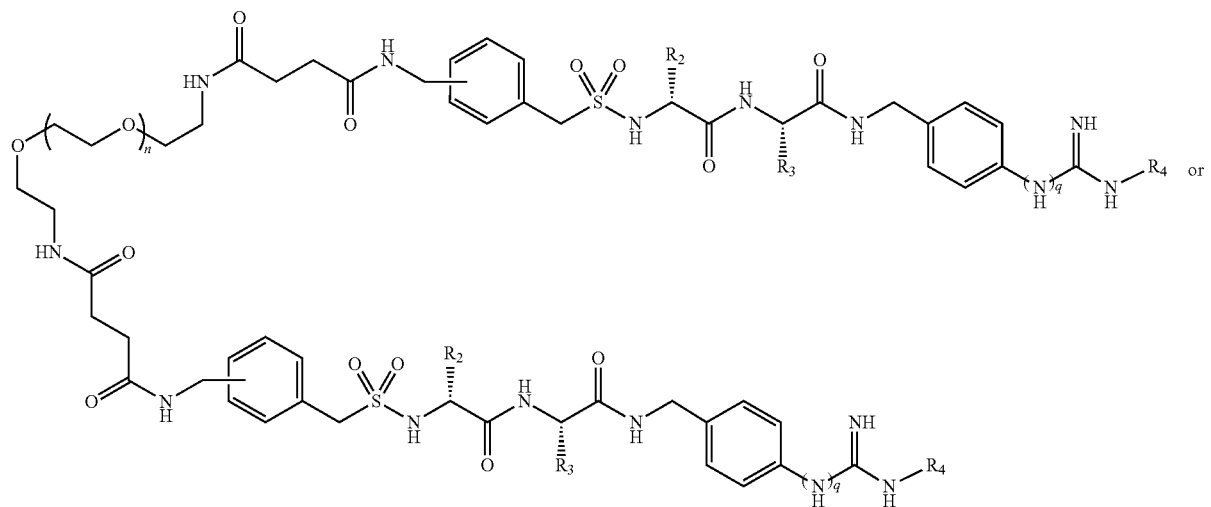
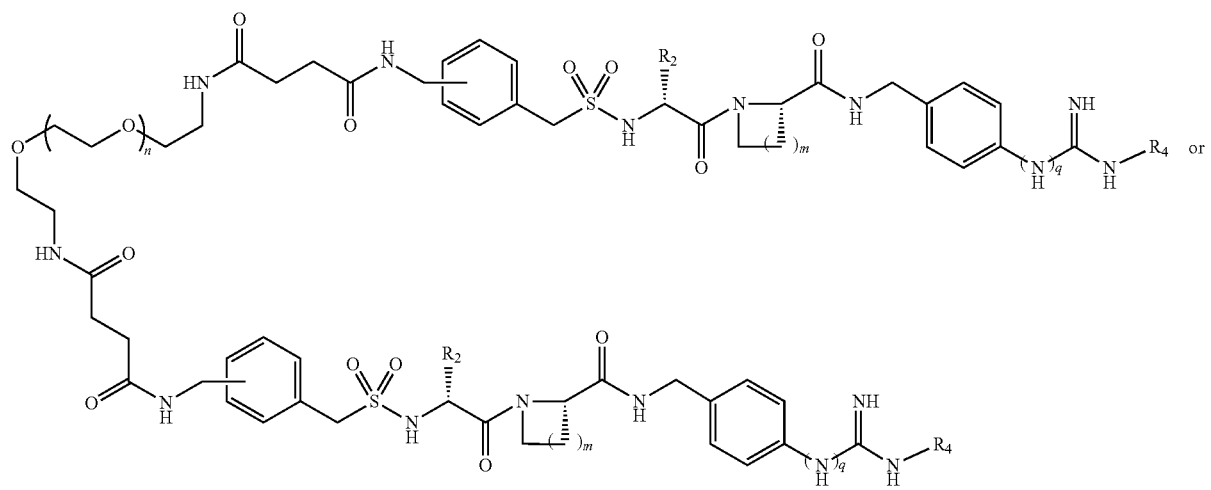

-continued

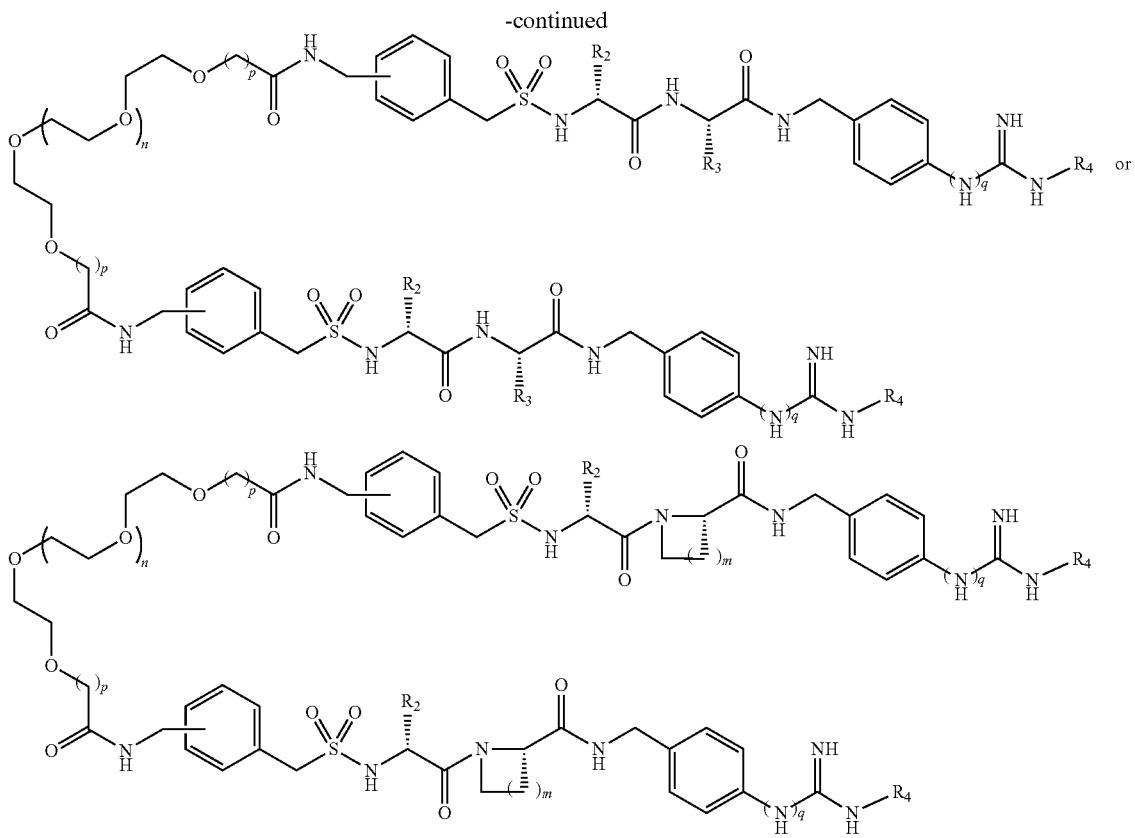

in which p=0, 1, 2 or 3, q=0 or 1, in particular 0, n=1 to 1000 and m=1 to 3, where $R_2$ and $R_3$ in each case have the above-mentioned meanings. Because of the absence of a second functional group, the above-listed substances can, aside from the covalent coupling to P4, only be coupled noncovalently to synthetic surfaces. This takes place by the oligo- or polyalkylene group of the linker group interacting with the synthetic surface.

Within the meaning of the present invention, interaction of the linker group, in particular of a linker group which contains an oligo- or polyalkylene group, with a synthetic surface is to be understood as meaning a noncovalent interaction of this linker group with the synthetic surface, for example by way of water-mediated hydrogen bonds, hydrophobic interactions or van der Waals' interactions.

Within the meaning of the present invention, the substances in which two molecules of the formula I are coupled to an oligo- or polyalkylene group are termed doubly inhibitor-functionalized oligo- or polyalkylene glycols.

Another advantage of oligo- and/or polyalkylene derivatives which are present as pure monomethyl ethers at one end, and are thus not suitable for covalent coupling, consists in their extended half-life in the circulation following systemic administration.

Preferred exemplary embodiments of acylated amidinobenzylamines in accordance with the general formula I having a linker group at P2 in accordance with the general formulae III and IV preferably exhibit one of the following structures:

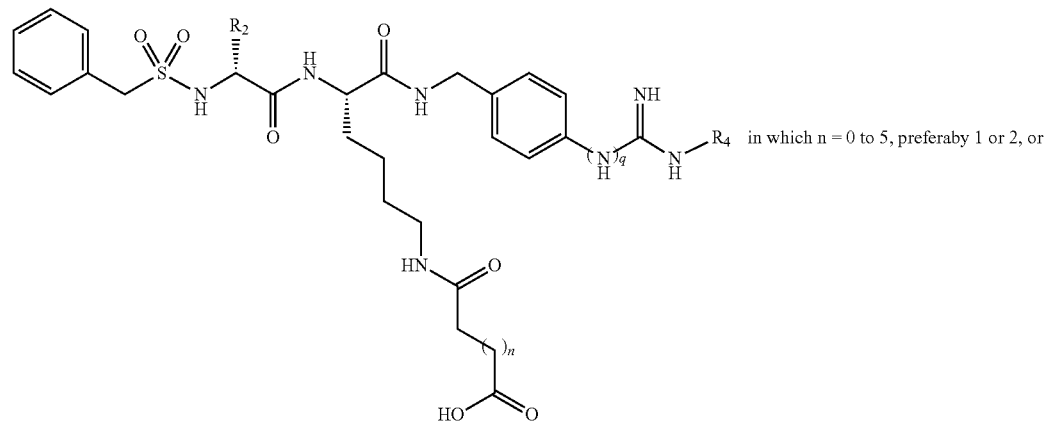

-continued
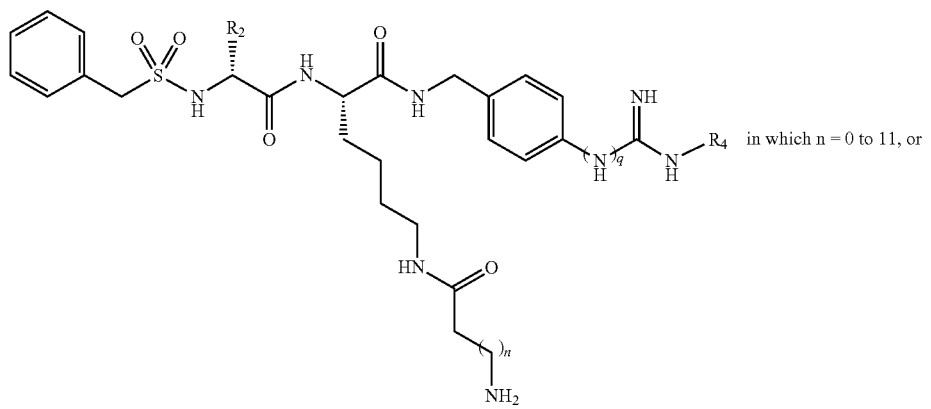
in which n = 0 to 11, or
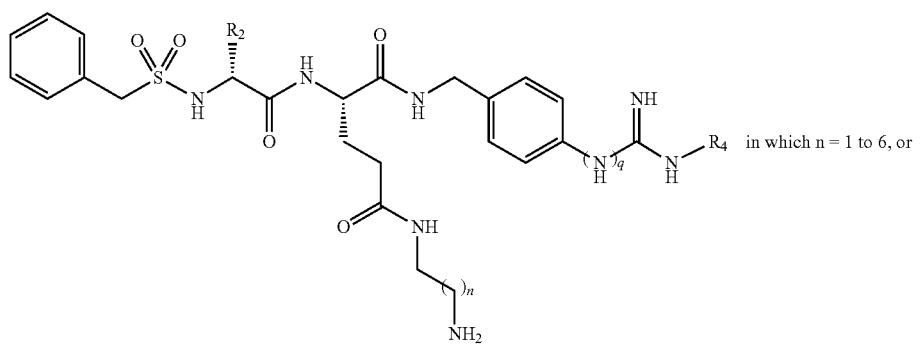
in which n = 1 to 6, or
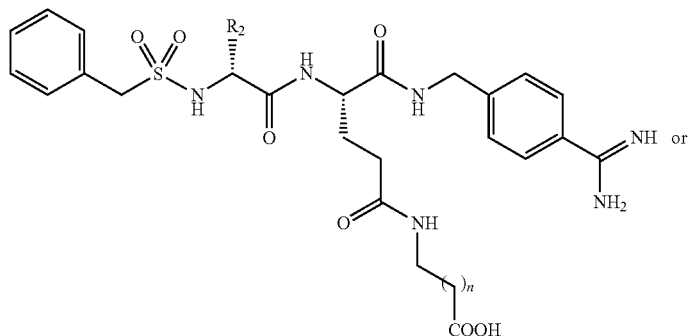
or
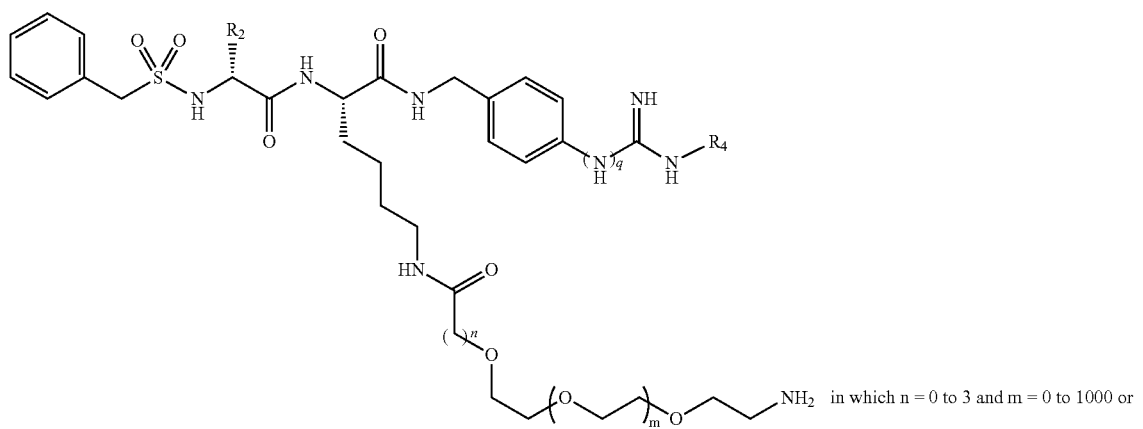
in which n = 0 to 3 and m = 0 to 1000 or -continued

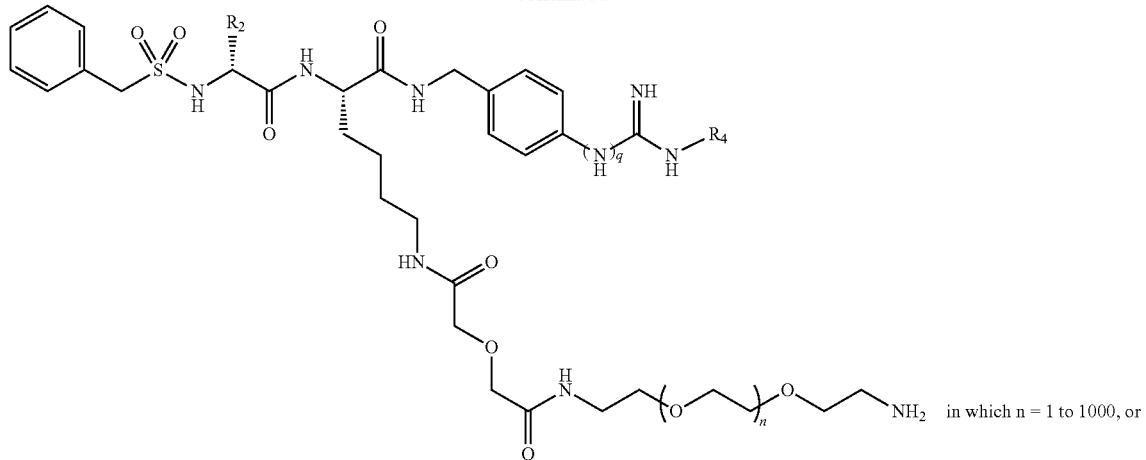

in which n = 1 to 1000, or

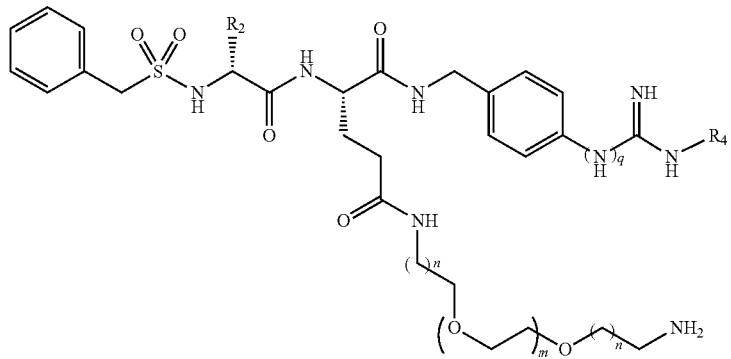

in which n=1 to 3 and m=1 to 1000, where q is in each case 0 or 1, in particular 0, and R₂ has in each case the abovementioned meanings. As a result of the presence of a second functional group, the above-listed substances can be coupled covalently to synthetic surfaces or to a second molecule of the general formula I concomitantly with the coupling to P2.

Another preferred exemplary embodiment of an acylated amidino- and/or guanidinobenzylamine in accordance with the general formula I having a linker group at P2 in accordance with the general formulae III and IV preferably exhibits one of the following structures:

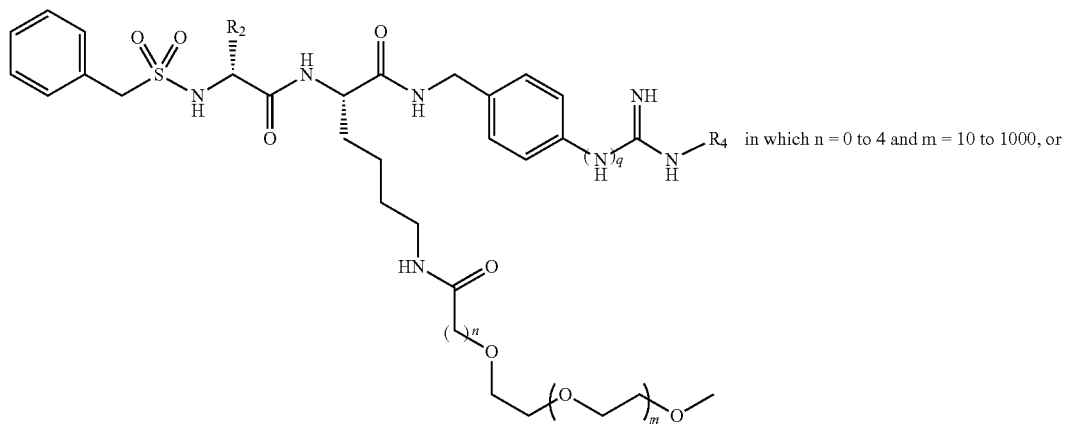

in which n = 0 to 4 and m = 10 to 1000, or

-continued
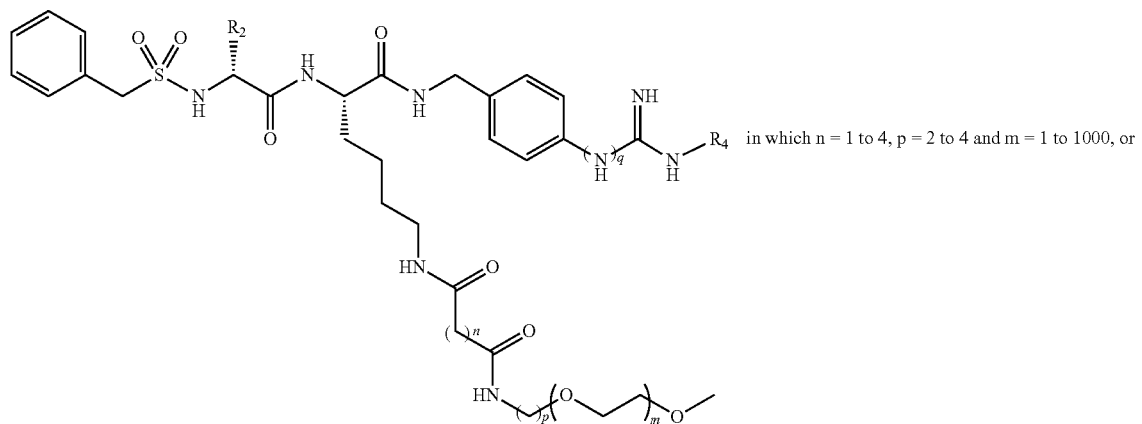 in which n = 1 to 4, p = 2 to 4 and m = 1 to 1000, or
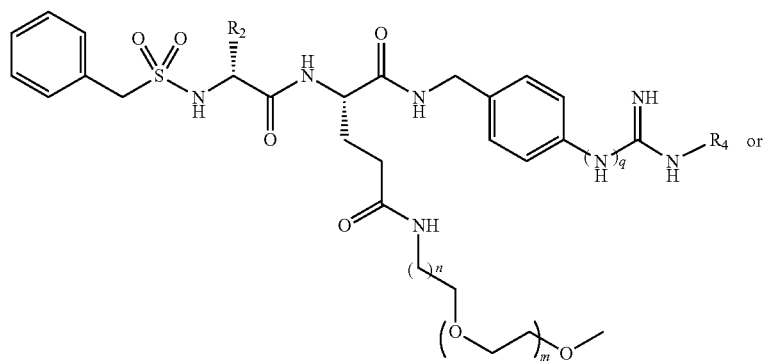 or
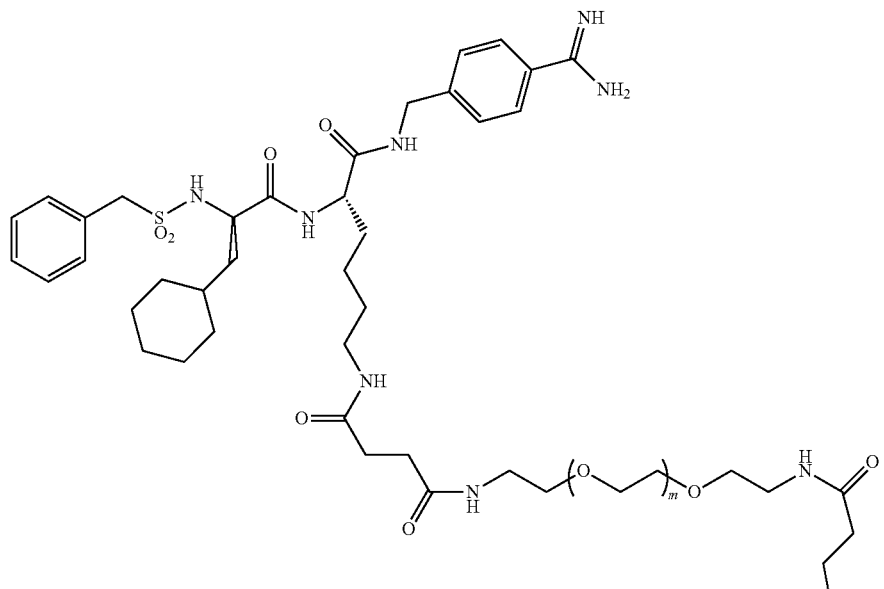

-continued

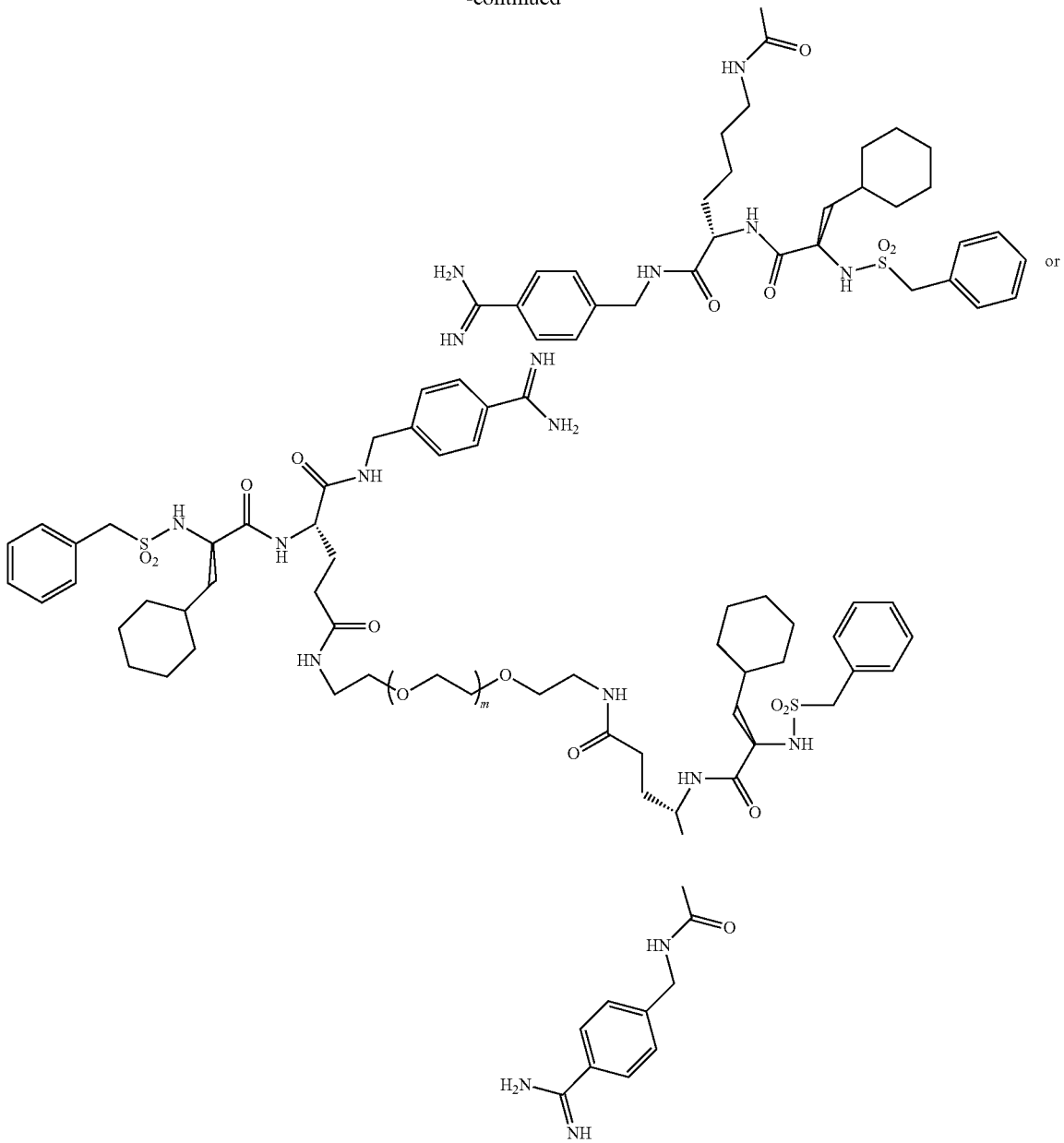

in which n=1 to 3 and m=10 to 1000, where q is 0 or 1, in particular 0, and $R_2$ in each case has the abovementioned meanings. As a result of the absence of a second functional group, the above-listed substances can, aside from the covalent coupling at P2, only be coupled noncovalently to synthetic surfaces. This takes place by means of the oligo- or polyalkylene group of the linker group interacting with the synthetic surface, for example on the basis of hydrogen bonds, hydrophobic interactions or van der Waals' interactions. Within the meaning of the present invention, the substances in which two molecules of the formula I are coupled to one oligo- or polyalkylene group are termed doubly inhibitor-functionalized oligo- or polyalkylene glycols.

Another advantage of these oligo- and/or polyalkylene derivatives which are present as pure monomethyl ethers at one end and are thus not suitable for covalent coupling consists, as in the case of the derivatives in which the linker group is coupled to P4, in their extended half-life in the circulation following systemic administration.

When the coupling to the synthetic surface takes place by way of P2, the substituent at P4 is, in particular, H, a halogen, an amino group, an hydroxyl group or a linear or branched alkyl group having from 1 to 6 carbon atoms.

A particularly preferred embodiment of an acylated amidinobenzylamine in accordance with the general formula I having a linker group at P4 in accordance with the general formula II preferably exhibits the following structure:

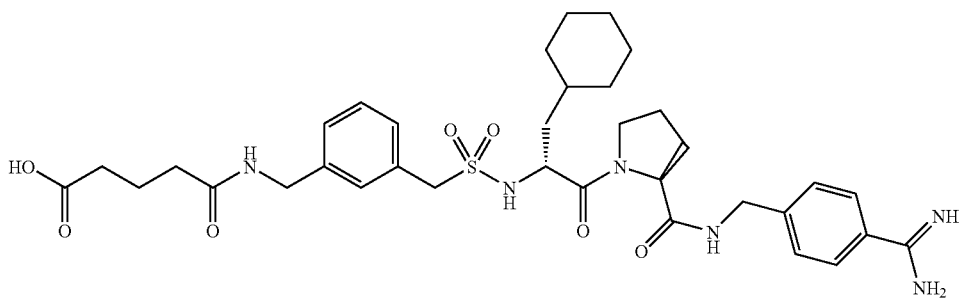

where D-Cha in position P3 can, in particular, also be D-Phe or D-Ser(tBu), and glutaryl at P4 can also be succinyl. This compound is suitable for simultaneous covalent coupling to a synthetic surface.

Another particularly preferred embodiment of an acylated amidinobenzylamine in accordance with the general formula I having a linker group at P2 in accordance with the general formulae III and IV preferably exhibits the following structure:

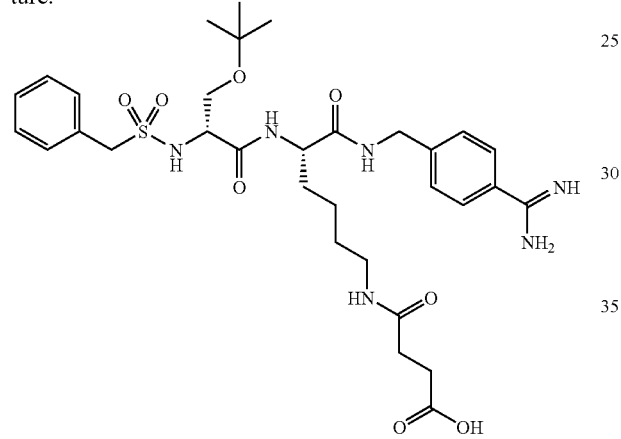

where D-Ser(tBu) in position P3 can, in particular, also be D-Cha or D-Phe, and succinyl at P2 can also be glutaryl. This compound is suitable for simultaneous covalent coupling to a synthetic surface.

Another particularly preferred embodiment of an acylated amidinobenzylamine in accordance with the general formula I having a linker group at P2 in accordance with the general formulae III and IV preferably exhibits one of the following structures:

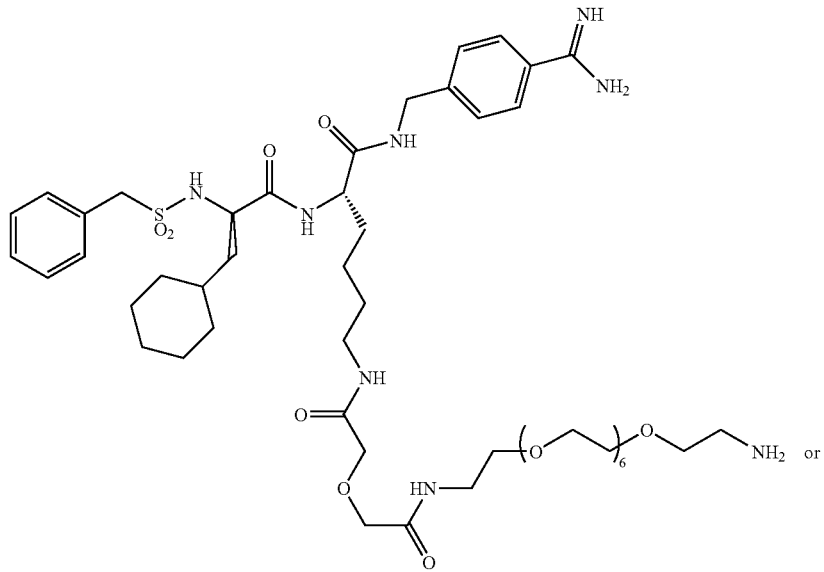

-continued

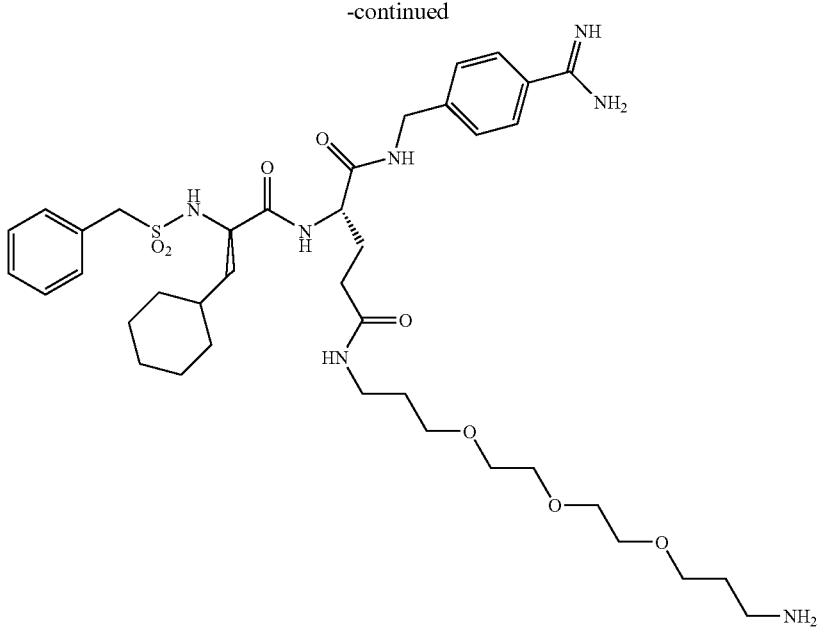

where D-Cha in position P3 can, in particular, also be D-Phe or D-Ser(tBu). These compounds are suitable for simultaneous covalent coupling to a synthetic surface or for covalent coupling to a second molecule of the general formula I.

Further possible exemplary embodiments of acylated aminobenzylamines which inhibit PK with high activity and specificity are compounds in accordance with formula I where P4 carries a radical R, P3 is D-Ser, D-Ser(tBu), D-Phe or D-Cha and P2 is a natural or unnatural amino acid Aaa, where R is H—, 4-, 3- or 2-, preferably 4- or 3-COOH, 4-, 3- or 2-, preferably 4- or 3-COOMe, 4-, 3- or 2-, preferably 4- or 3-AMe, 4-, 3- or 2-, preferably 4- or 3-glutaryl-AMe or 4-, 3- or 2-, preferably 4- or 3-CN, and Aaa is Gly, Ala, Pro, Asp, Glu, Gln, hGlu, Dap, Dap(Z), Lys, Lys(Z), Arg, Thr, Thr(Bzl), Ser, Ser(Bzl), hSer, hSer(Bzl), Phe or hPhe.

In this connection, particular preference is given to the acylated aminobenzylamines where, when P3 is D-Ser, Aaa is preferably Gln, Dap, Dap(Z), Lys, Lys(Z), Ser(Bzl), hSer, Phe or hPhe, in particular Lys(Z), and R is H or, when Aaa is Ala or Ser, R is HOOC—;

or, when P3 is D-Ser(tBu), Aaa is Pro, Gln, Dap, Dap(Z), Lys, Lys(Z), Arg, Thr, Thr(Bzl), Ser(Bzl), hSer(Bzl), Phe or hPhe, in particular Pro, Gln, Lys, Lys(Z), hSer(Bzl), Phe or hPhe, and R is H or, when Aaa is Gly or Ala, R is HOOC— or, when Aaa is Pro, R is CN—;

or, when P3 is D-Cha, Aaa is Lys or Glu and R is H or, when Aaa is Pro, R is glutaryl-AMe, in particular, when Aaa is —NH—CH—[CH$_2$—CH$_2$—CO—NH—(CH$_2$)$_3$—[O—(CH$_2$)$_2$]$_3$—CH$_2$—NH$_2$]—CO—, R is H.

As a rule, the acylated 4-amidino- or 4-guanidinobenzylamine derivatives according to the invention are present in the form of a salt, in particular of a mineral acid, for example sulfuric acid or hydrochloric acid, or of a suitable organic acid, for example acetic acid, formic acid, methylsulfonic acid, succinic acid, malic acid or trifluoroacetic acid, in particular as hydrochloride, sulfate or acetate.

Another preferred embodiment of the present invention is the reaction of an H$_2$N group of a linker group coupled to the acylated 4-amidino- or 4-guanidinobenzylamine with a dicarboxylic anhydride, preferably the anhydride of succinic acid or of glutaric acid, with the formation of an HOOC— group, or the reaction of an HOOC— group of a linker group coupled to the acylated 4-amidino- or 4-guanidinobenzylamine with a diamine with the formation of an H$_2$N group. These reactions are carried out using standard methods which are known to the skilled person.

The conversion of an H$_2$N group into an HOOC— group, and of an HOOC— group into an H$_2$N group, which these reactions make possible extends the opportunities for coupling the compounds of the general formula I to synthetic surfaces or to a second molecule of the general formula I.

In a particularly preferred embodiment of the present invention, the linker group which is coupled covalently to P4 or P2 can, in the presence of a second functional group, in particular a substituted or unsubstituted amino, carboxyl and/or mercapto group, be simultaneously coupled covalently to synthetic surfaces or, provided the linker group is an oligo- or polyalkylene glycol, coupled covalently to a second molecule of the general formula I with the formation of a doubly inhibitor-functionalized oligo- or polyalkylene glycol termed.

According to a preferred embodiment of the present invention, the synthetic surface to which the acylated 4-amidino- or 4-guanidinobenzylamine derivatives can be coupled is composed of cellulose diacetate, cellulose triacetate, poly(ether sulfone), poly(aryl ether sulfone), regenerated cellulose, cuprophan, hemophan, poly(sulfone), poly(acrylonitrile), poly(vinyl alcohol), poly(carbonate), poly(amide), poly(methyl methacrylate), poly(ethylene-co-vinyl alcohol) or another material which is used in appliances such as dialyzers, oxygenators, catheters or membranes, and/or the hose systems and/or air traps which belong to the appliances, for the surfaces which come into contact with blood, with the surface material, for the covalent coupling of the molecule of the general formula I by way of the linker group coupled to P4 or P2, being modified, where appropriate, with functional groups, e.g. amino groups, aminoalkyl groups, carboxyl groups, carboxyalkyl groups, mercapto groups, mercaptoalkyl groups, hydroxyl groups or hydroxyalkyl groups, with the alkyl radical exhibiting 1-10, in particular 1-6, C atoms.

According to another preferred embodiment of the present invention, the acylated 4-amidino- or 4-guanidinobenzylamine derivatives are coupled to synthetic surfaces of, for example, appliances such as dialyzers, oxygenators, catheters and/or membranes for the purpose of preventing blood coagulation at the surfaces of these appliances.

The coupling of the acylated 4-amidino- or 4-guanidinobenzylamine derivatives is preferably effected by covalently or noncovalently coating the synthetic surface(s) by way of one of the above-described linker groups which is bonded to a substituent on P4 and/or where appropriate bonded directly to the side chain of P2 of the general formula I.

Within the meaning of the present invention, an appliance is any device which comes into contact with blood and its constituents.

Another preferred embodiment of the present invention is the use of one or more of the acylated 4-amidino- or 4-guanidinobenzylamine derivatives according to the invention for producing a pharmaceutical for use as an anticoagulant and/or antithrombotic agent for preventing and/or treating cardiac infarction, cerebral stroke, embolisms, deep leg vein thromboses, e.g. following hip joint operations and/or knee joint replacement, unstable angina, and complications as a consequence of angioplasty, in particular percutaneous transluminal coronary angioplasty (PTCA).

Within the meaning of the present invention, anticoagulant is to be understood as meaning any substance which inhibits blood coagulation. Within the meaning of the present invention, antithrombotic agents are to be understood as being substances which are to be used in thrombosis prophylaxis. Within the meaning of the present invention, angioplasty is to be understood as meaning a dilatation of blood vessels, in particular using catheters such as balloon catheters.

Another embodiment is the use of one or more of the above-described acylated 4-amidino- or 4-guanidinobenzylamines for producing a pharmaceutical for use as an anticoagulant and/or antithrombotic agent for the purpose of preventing and treating disseminated intravascular coagulation, septic shock, allergies, the postgastrectomy syndrome, arthritis and ARDS (adult respiratory distress syndrome).

According to a preferred embodiment of the present invention, the acylated 4-amidino- or 4-guanidinobenzylamine derivatives are used for producing a pharmaceutical for inhibiting plasma kallikrein and/or factor XIa and/or factor XIIa in a parenteral use form, in particular in an intraarterial, intravenous, intramuscular or subcutaneous form, in an enteral use form, in particular for oral or rectal use, or in topical use form, in particular as a skin treatment agent. Preference is given to intravenous or subcutaneous use forms in this connection. The inhibition of plasma kallikrein is preferred, for example.

The acylated 4-amidino- or 4-guanidinobenzylamine derivatives according to the invention can be used, in particular, for producing a pharmaceutical for inhibiting plasma kallikrein, which pharmaceutical is in the form of a tablet, a sugar-coated tablet, a capsule, a pellet, a suppository, a solution, in particular a solution for injection or infusion, of eye, nose and ear drops, of a juice, of a capsule, of an emulsion or suspension, of globuli, of styli, of an aerosol, of a powder, of a paste, of a cream or of an ointment.

In addition to the inhibitor according to the invention, the pharmaceutical can comprise further pharmaceutically suitable auxiliary substances and/or additives. Suitable auxiliary substances and/or additives which serve, for example, to stabilize and/or preserve the pharmaceutical are well-known to the skilled person (e.g. Sucker H. et al., (1991) Pharmazeutische Technologie [Pharmaceutical technology], 2nd edition, Georg Thieme Verlag, Stuttgart). They include, for example, physiological sodium chloride solutions, Ringer glucose, Ringer lactate, demineralized water, stabilizers, antioxidants, complexing agents, antimicrobial compounds, proteinase inhibitors and/or inert gases.

Another embodiment of the present invention is the use of acylated amidinobenzylamine of the general formula V or VI, in which $R_4$ is, in particular, HO— and $R_1$ and $R_3$ are not an oligo- or polyalkylene group, for producing a pharmaceutical for use as an anticoagulant and/or antithrombotic agent in connection with the abovementioned indications, with the active compound being present in the form of a prodrug for oral administration.

Within the meaning of the present invention, a prodrug according to the general formula I which is present as a pharmaceutically inactive derivative of the corresponding pharmaceutically active substance and, after having been administered orally, is biotransformed spontaneously or enzymically with the pharmaceutically active substance being released.

In addition to the preferred use of the described acylated amidino- or guanidinobenzylamines for inhibiting plasma kallikrein, they can also be used for inhibiting other trypsin-like serine proteases such as thrombin, factor XIIa, factor XIa, Xa, factor IXa, factor VIIa, urokinase, tryptase and plasmin as well as trypsin-like serine proteases of the complement system.

The present invention also relates to acylated 4-amidino- or 4-guanidinobenzylamine in accordance with the general formula P4-P3-P2-P1 (I), with the substance being bound, covalently or noncovalently, to a synthetic surface by way of one of the above-described linker groups at P4 and/or at P2. In this connection, the substance is preferably bound covalently to a synthetic surface by way of an amide or sulfonamide bond, a disulfide bridge or the alkylation of a mercapto group, in particular by way of an amide bond. The substance is bound noncovalently to a synthetic surface preferably by way of an oligo- or polyalkylene glycol group, in particular an oligo- or polyethylene glycol group, interacting with a synthetic surface.

The present invention also relates to a synthetic surface, with the surface being coated covalently or noncovalently with an acylated 4-amidino- or 4-guanidinobenzylamine according to the invention. The present invention also relates to an appliance, for example a dialyzer, oxygenator, catheter or a membrane, together with the appurtenant hose systems and/or air traps, which contains a synthetic surface which is covalently or noncovalently coated with an acylated 4-amidino- or 4-guanidinobenzylamine according to the invention.

The acylated 4-amidino- or 4-guanidinobenzylamine derivatives according to the invention are synthesized using methods known to the skilled person. For example, methods known to the skilled person are used to obtain Boc-protected 4-(acetyloxamidino)benzylamine from the commercially obtainable 4-cyanobenzylamine (Showa Denko, Japan). Another possibility is that of directly coupling 4-cyanobenzylamine to the Boc- or Z-protected P2 amino acid and converting the cyano group into the acetyloxamidine at this stage. After the Boc protecting group has been eliminated, standard coupling methods are used to couple on the other amino acids using Boc as the N-terminal protecting group. The P3 amino acid can also be coupled directly as an N-aryl- or N-aralkylsulfonyl-protected amino acid. Most of the intermediates crystallize well and can be readily purified in this way. The inhibitors are finally purified at the last stage, preferably by way of preparative, reversed-phase HPLC.

In that which follows, the invention will be explained in more detail, without this restricting it, with the aid of the appended exemplary embodiments and tables.

| Abbreviations employed | |
|---|---|
| Aaa | amino acid |
| Ac | acetyl |
| AcOH | acetic acid |
| CNA | acetonitrile |
| Amba | amidinobenzylamine |
| AMe | aminomethyl |
| ARDS | adult respiratory distress syndrome |
| Boc | tert-butyloxycarbonyl |
| Bzl | benzyl |
| Bzls | benzylsulfonyl |
| Can | canavanine |
| Cha | cyclohexylalanine |
| IBCC | isobutyl chlorocarbonate |
| CNBzls | cyanobenzylsulfonyl |
| Dab | α,γ-diaminobutyric acid |
| Dap | α,β-diaminopropionic acid |
| Dap(Z) | benzyloxycarbonyl-α,γ-diaminobutyric acid |
| DCM | dichloromethane |
| DIEA | diisopropylethylamine |
| DMF | N,N-dimethylformamide |
| D-Ser | D-serine, other amino acids correspondingly |
| D-Ser(tBu) | D-(tert-butylserine) |
| F XIa | factor XIa |
| F XIIa | factor XIIa |
| Glut | glutaryl |
| GuMe | guanidinomethylene |
| hAla(4-Pyr) | homo-4-pyridylalanine |
| 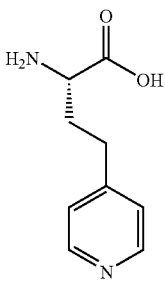 [SMILES: N[C@@H](CCc1ccncc1)C(=O)O] | |
| hGlu | beta-homoglutamic acid |
| 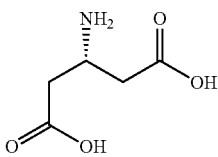 | |
| hPhe | homophenylalanine |
| 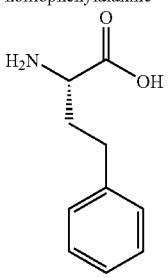 | |

| -continued | |
|---|---|
| Abbreviations employed | |
| hSer | beta-homoserine |
| 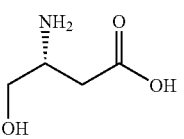 | |
| hTyr | homotyrosine |
| 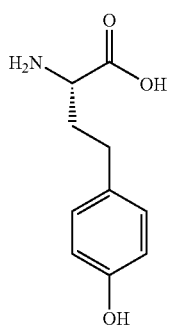 | |
| n.d. | not determined |
| PEG | polyethylene glycol |
| Phe | phenylalanine |
| PK | plasma kallikrein |
| Pro-MMP 3 | pro-matrix metalloprotease 3 |
| PyBop | benzotriazol-1-yl-N-oxytris(pyrrolidino)phosphonium hexafluorophosphate |
| RT | room temperature |
| Ser(Blz) | serine(benzyl) |
| Suc | succinyl |
| TFA | trifluoroacetic acid |
| Tfa | trifluoroacetyl |
| Z | benzyloxycarbonyl |

Analytical Methods:

Analytical HPLC: Shimdazu LC-10A system, column: Phenomenex Luna $C_{18}$, 5 μm (250×4 mm), solvent A: 0.1% TFA in water; B: 0.1% B in ACN, gradient: 10% B to 70% B in 60 min, 1 ml/min flow rate, detection at 220 nm.

Preparative HPLC: Shimdazu LC-8A system, column: Phenomenex Luna $C_{18}$, 5 μm (250×30 mm), solvent A: 0.1% TFA in water; B: 0.1% B in ACN, gradient: 10% B to 55% B in 120 min, 10 ml/min flow rate, detection at 220 nm.

Mass spectroscopy: The mass spectra were either measured on a Kompact probe from Kratos (Manchester, UK) using a time of flight measurement detector and α-cyanohydroxycinnamic acid as matrix or using an ESI-MS LCQ from Finnigan (Bremen, Germany).

EXEMPLARY EMBODIMENT 1

Synthesizing 3-(glutarylamidomethyl)benzylsulfonyl-D-Cha-Pro-4-amidinobenzylamide×TFA The combined ethyl acetate phase was washed, in each case 3×, with a 5% solution of $KHSO_4$ and a saturated solution of NaCl and then dried over $Na_2SO_4$. The solvent was removed in vacuo.

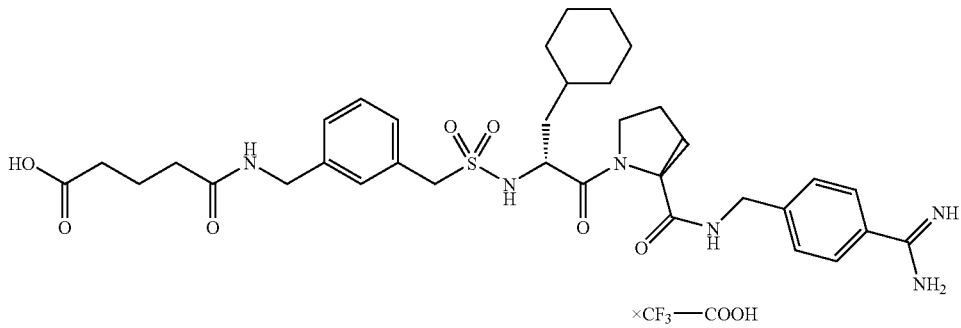

1a) 3-(Cyano)benzylsulfonic Acid, Sodium Salt 30 g (153 mmol) of 3-cyanobenzyl bromide (Aldrich) were suspended in 150 ml of water and boiled under reflux for 8 h after 21.2 g (168.3 mmol) of $Na_2SO_3$ had been added. The mixture was filtered in the hot state and the water was evaporated to some degree in vacuo. The mixture was stored in a refrigerator overnight for crystallization; after that, the crystals were filtered off with suction and recrystallized once again from water. The crystals were filtered off with suction and dried in vacuo.

Yield: 17.1 g (78 mmol), HPLC: 18.2% B

1b) 3-(Cyano)benzylsulfonyl Chloride 5 g (22.83 mmol) of 3-cyanobenzylsulfonic acid sodium salt were moistened with approx. 20 ml of phosphoryl chloride, after which 5.2 g (25.11 mmol) of $PCl_5$ were added and the mixture was stirred for 15 min while being cooled with ice. The mixture was then heated at 80° C. for 4 h. After that, the mixture was poured onto ice and stirred vigorously for 30 min in connection with which the product sedimented as a white solid on the ice. After the ice had been partially thawed, the mixture was filtered through a frit and the product/ice mixture which remained was washed several times with water. The crystals which remained were dried in vacuo and used directly for the next step in the synthesis.

Yield: 3.4 g (15.8 mmol)

1c) 3-(Cyano)benzylsulfonyl-D-Cha-OH 3.775 g (22 mmol) of H-D-Cha-OH were suspended in 100 ml of dry DCM after which 6.316 ml (50 mmol) of trimethylsilyl chloride and 8.7 ml (50 mmol) of DIEA were added. The mixture was boiled under reflux for 1 h and cooled in an ice bath. 5 g (23.18 mmol) of 3-cyanobenzylsulfonyl chloride and 5 ml (28.75 mmol) of DIEA were then added within the space of 30 min. The mixture was stirred for a further 30 min while being cooled with ice and then stirred for a further 3 h at room temperature. The solvent was removed in vacuo after which the residue was dissolved in water (brought to pH 8.5-9 with 1 N NaOH) and this solution was extracted 2× with ethyl acetate. The ethyl acetate phase was then extracted once again with alkaline water (pH 9, NaOH). The combined alkaline water phases were then acidified (pH approx. 3) with a concentrated solution of HCl and extracted 3× with ethyl acetate.

Yield: 6.99 g of oil which crystallizes slowly in the refrigerator, HPLC: 53.9% B

1d) H-Pro-4-(Acetyloxamidino)benzylamide×HBr 75 ml of HBr solution (33% strength in acetic acid) were added, at room temperature, to 5 g of Z-Pro-4-(acetyloxamidino)benzylamide (synthesized as described in WO 02/059065). The mixture was left to stand for one hour while being shaken occasionally. After that, ether was added to the mixture and the precipitated product was filtered off with suction and washed several times on the frit with ether. The product was dried in vacuo.

Yield: 4.3 g (11.16 mmol), HPLC 18.3% B

1e) 3-(Cyano)benzylsulfonyl-D-Cha-Pro-4-(acetyloxamidino)benzylamide 2.5 g (7.13 mmol) of 3-cyanobenzylsulfonyl-D-Cha-OH and 2.74 g (7.13 g) of H-Pro-4-(acetyloxamidino)benzylamide×HBr were dissolved in 50 ml of DMF. 3.71 g (7.13 mmol) of PyBop and 3.7 ml of DIEA were added while cooling with ice. The mixture was stirred for 30 min while being cooled with ice and then stirred at RT for 3 h. The solvent was removed in vacuo after which the mixture was taken up in ethyl acetate and this solution was washed, in each case 3×, with 5% $KHSO_4$, NaCl-saturated water, a saturated solution of $NaHCO_3$ and, once again, with NaCl-saturated water. The ethyl acetate phase was dried with $Na_2SO_4$ and the solvent was then removed in vacuo. The crude product was used without any further purification for the next step in the synthesis.

Yield: 3.3 g of oil, HPLC at 53.77% B

MS: calculated 578.27 (monoisotopic). found 579.4 $[M+H]^+$.

1f) 3-(Aminomethyl)benzylsulfonyl-D-Cha-Pro-4-(amidino)benzylamide×2 HCl 1 g of 3-cyanobenzylsulfonyl-D-Cha-Pro-4-(acetyloxamidino)benzylamide crude product was dissolved in 500 ml of acetic acid after which 150 ml of 1 N HCl were added. After that, 200 mg of catalyst (10% palladium on active charcoal) were added and the mixture was hydrogenated with hydrogen at 50° C. for 15 h. The catalyst was filtered off and the solvent was evaporated in vacuo. Toluene was added to the residue and the solvent was removed in vacuo; the procedure was repeated a further 2×. The residue was dissolved in a little methanol and the product was precipitated by adding ether and filtered off with suction. The product was washed with ether and dried in vacuo. The crude product was used without further purification for the next step in the synthesis.

Yield: 0.8 g, HPLC at 34.28% B

MS: calculated 582.30 (monoisotopic). found 583.5 [M+H]$^+$.

1 g) 3-(Glutarylamidomethyl)benzylsulfonyl-D-Cha-Pro-4-(amidino)benzylamide×TFA 38 mg (0.33 mmol) of glutaric anhydride and 115 µl (0.66 mmol) of DIEA in 5 ml of DMF were added, while cooling with ice, to 200 mg (approx. 0.3 mmol) of 3-(aminomethyl) benzylsulfonyl-D-Cha-Pro-4-(amidino)benzylamide×2 HCl crude product. The mixture was stirred for 30 min while being cooled with ice and then stirred for a further 3 h at RT. The solvent was removed in vacuo and the crude product was purified by means of preparative reversed-phase HPLC.

Yield: 125 mg, HPLC at 40.1% B

MS: calculated 696.33 (monoisotopic). found 697.8 [M+H]$^+$.

EXEMPLARY EMBODIMENT 2

Synthesizing benzylsulfonyl-D-Ser(tBu)-Lys(succinyl)-4-Amba×TFA

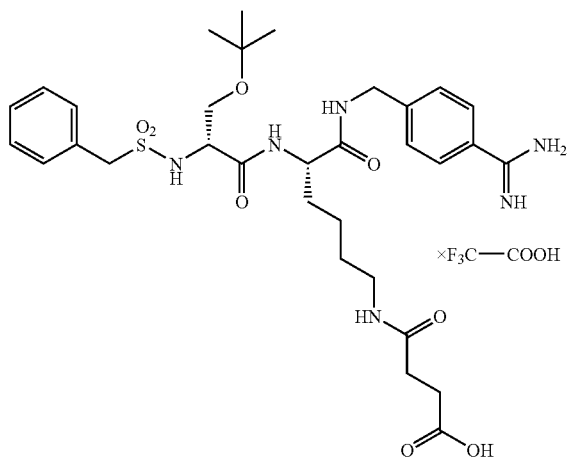

2a) Boc-Lys(Tfa)-4-(acetyloxamidino)benzylamide 5 g (14.61 mmol) of Boc-Lys(Tfa)-OH were dissolved in 100 ml of THF after which 1.767 ml (16.10 mmol) of NMM and 1.899 ml (14.61 mmol) of IBCC were added at −15° C. The mixture was stirred at −15° C. for 10 min after which 3.74 g (15.33 mmol) of 4-(acetyloxamidino)benzylamine×HCl (prepared as described in WO 01/96282 A2) and, once again, 1.767 ml (16.10 mmol) of NMM were added. The mixture was stirred for a further hour at −15° C. and then overnight at room temperature. The solvent was removed in vacuo and the mixture was taken up in ethyl acetate; this solution was then washed, in each case 3×, with 5% KHSO$_4$, NaCl-saturated water, a saturated solution of NaHCO$_3$ and, once again, with NaCl-saturated water and then dried with Na$_2$SO$_4$. The solvent was removed in vacuo and the product was crystallized from ethyl acetate.

Yield: 6.82 g (12.83 mmol) of white crystals, HPLC: 43.87% B

2b) H-Lys(Tfa)-4-(Acetyloxamidino)benzylamide× HCl 5 g (9.41 mmol) of Boc-Lys(Tfa)-4-(acetyloxamidino) benzylamide were solubilized in a little glacial acetic acid after which 100 ml of 1 N HCl in glacial acetic acid were added. After the mixture had been standing at room temperature for 45 min, part of the solvent was evaporated off and the product was precipitated by adding diethyl ether; it was then filtered off with suction and washed again with diethyl ether. The product was dried in vacuo.

Yield: 4.65 g (10.78 mmol) of white solid, HPLC: 25.52% B

2c) Bzls-D-Ser(tBu)-Lys(Tfa)-4-(Acetyloxamidino) benzylamide 1.93 g (6.107 mmol) of Bzls-D-Ser(tBu)-OH and 3 g (6.412 mmol) of H-Lys(Tfa)-4-(acetyloxamidino)-benzylamide×HCl were dissolved in 30 ml of acetonitrile after which 3.337 g (6.412 mmol) of PyBop and 3.187 ml (18.32 mmol) of DIEA were added at 0° C. The mixture was stirred for 30 min at 0° C. and for a further 4 h at room temperature. The solvent was removed in vacuo and the residue was taken up in ethyl acetate; this solution was then washed, in each case 3×, with 5% KHSO$_4$, NaCl-saturated water, a saturated solution of NaHCO$_3$ and, once again, with NaCl-saturated water and then dried with Na$_2$SO$_4$. The solvent was removed in vacuo. A slightly yellow, amorphous crude product remained, with this product being used directly, without further purification, for the next step in the synthesis.

Yield: 5.88 g (crude product), HPLC: 52.93% B

2d) Bzls-D-Ser(tBu)-Lys(Tfa)-4-(Amidino)benzylamide×acetate 5.88 g of Bzls-D-Ser(tBu)-Lys(Tfa)-4-(acetyloxamidino) benzylamide (crude product) were dissolved in 150 ml of 90% acetic acid after which 500 mg of catalyst (10% Pd/C) were added. The mixture was hydrogenated with hydrogen for 6 h, at room temperature and under standard pressure. The catalyst was then filtered off and the solvent was partially evaporated; the product was then precipitated, by adding diethyl ether, filtered off with suction and washed once again with diethyl ether. The white crystalline precipitate was dried in vacuo.

Yield: 4.36 g (5.962 mmol), HPLC: 43.50% B

2e) Bzls-D-Ser(tBu)-Lys-4-(Amidino)benzylamide×2 TFA 5 ml of a 1 M aqueous solution of piperidine were added, while cooling with ice, to 0.2 g of Bzls-D-Ser(tBu)-Lys(Tfa)-4-(amidino)benzylamide×acetate crude product and the mixture was stirred for 3 h. After that, the solvent was evaporated off in vacuo and the remaining residue was purified by means of preparative reversed-phase HPLC.

Yield: 72 mg, HPLC: 30.9% B

MS: calculated 574.29 (monoisotopic). found 575.7 [M+H]$^+$.

2f) Bzls-D-Ser(tBu)-Lys(Succinyl)-4-(amidino)benzylamide×TFA 2 ml of DMF, 7.8 mg (0.078 mmol) of succinic anhydride and 27.1 µl (0.156 mmol) of DIEA were added, while cooling with ice, to 60 mg (0.075 mmol) of Bzls-D-Ser(tBu)-Lys-4-(amidino)benzylamide×2 TFA. The mixture was stirred for a further 30 min while being cooled with ice and then for 3 h at room temperature. The solvent was removed in vacuo and the product was purified by means of preparative reversed-phase HPLC.

Yield: 41 mg, HPLC: 35.8% B

MS: calculated 674.31 (monoisotopic). found 675.9 $[M+H]^+$.

EXEMPLARY EMBODIMENT 3

Synthesizing benzylsulfonyl-D-Cha-Lys (CO—CH$_2$—O—CH$_2$—CO—NH—CH$_2$—CH$_2$-hexaethylene glycol-CH$_2$—CH$_2$—NH$_2$)-4-Amba×2 TFA

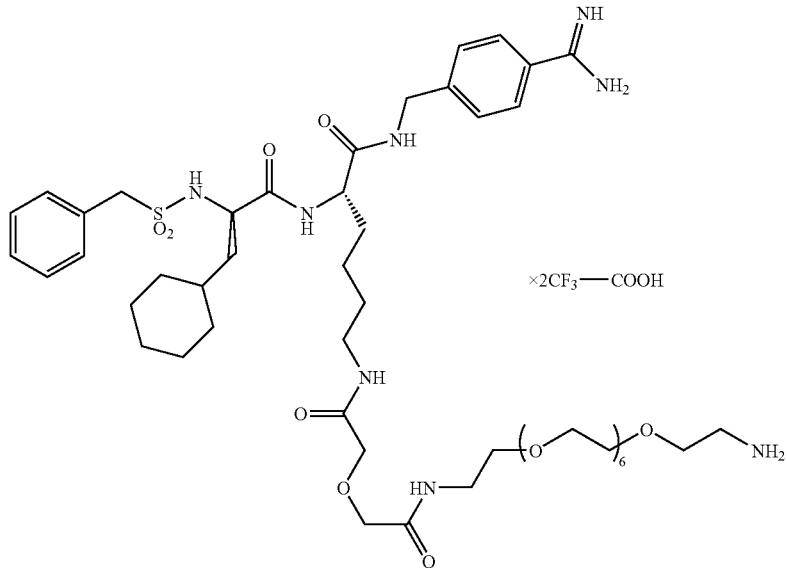

3a) Benzylsulfonyl-D-Cha-OH 6 g (35.1 mmol) of H-D-Cha-OH were suspended in 120 ml of dry DCM after which 9.75 ml (77.2 mmol) of trimethylsilyl chloride and 13.4 ml (77.2 mmol) of DIEA were added. The mixture was boiled under reflux for 1 h and then cooled in an ice bath. 7.02 g (36.85 mmol) of benzylsulfonyl chloride and 7.83 ml (45 mmol) of DIEA were then added within the space of 30 min. The mixture was stirred for a further 30 min while being cooled with ice and, after that, for a further 3 h at room temperature. The solvent was removed in vacuo and the residue was dissolved in water (brought to pH 8.5-9 with 1 N NaOH); this solution was then extracted 2× with ethyl acetate. The alkaline aqueous phase was then acidified (pH approx. 3) with a concentrated solution of HCl and extracted 3× with ethyl acetate. The combined ethyl acetate phase was washed, in each case 3×, with a 5% solution of KHSO$_4$ and an NaCl-saturated solution and then dried with Na$_2$SO$_4$. The solvent was removed in vacuo.

Yield: 9.2 g of oil (crystallizes slowly in the refrigerator), HPLC: 55.8% B

3b) Boc-Lys(Z)-4-(Acetyloxamidino)benzylamide 4.41 g (11.59 mmol) of Boc-Lys(Z)—OH were dissolved in 125 ml of DMF after which 1.275 ml (11.59 mmol) of NMM and 1.506 ml (11.59 mmol) of IBCC were added at −15° C. The mixture was stirred at −15° C. for 10 min after which 2.97 g (12.17 mmol) of 4-(acetyloxamidino)benzylamine×HCl (prepared as described in WO 01/96286 A2) and, once again, 1.34 ml (12.17 mmol) of NMM were added. The mixture was stirred for a further hour at −15° C. and overnight at room temperature. The solvent was removed in vacuo and the mixture was taken up in ethyl acetate; this solution was then washed, in each case 3×, with 5% KHSO$_4$, NaCl-saturated water, a saturated solution of NaHCO$_3$ and, once again, with NaCl-saturated water and then dried with Na$_2$SO$_4$. The solvent was removed in vacuo and the amorphous substance which remained was dried in vacuo.

Yield: 5.2 g, HPLC: 51.12% B

3c) H-Lys(Z)-4-(Acetyloxamidino)benzylamide×HCl 100 ml of 1 N HCl in glacial acetic acid were added to 5 g of Boc-Lys(Z)-4-(acetyloxamidino)benzylamide. After the mixture had been standing at room temperature for 45 min, the solvent was partially evaporated and the product was precipitated by adding diethyl ether; it was then filtered off with suction and washed once again with diethyl ether. The product was dried in vacuo.

Yield: 4.2 g (8.3 mmol) of white solid, HPLC: 33.81% B

3d) Bzls-D-Cha-Lys(Z)-4-(acetyloxamidino)benzylamide 2 g (6.146 mmol) of Bzls-D-Cha-OH and 3.13 g (6.146 mmol) of H-Lys(Z)-4-(acetyloxamidino)benzylamide×HCl were dissolved in 50 ml of DMF after which 3.198 g (6.146 mmol) of PyBop and 3.2 ml (18.43 mmol) of DIEA were added at 0° C. The mixture was stirred for 30 min at 0° C. and for a further 5 h at room temperature. The solvent was removed in vacuo and the residue was taken up in ethyl acetate; it was then washed, in each case 3×, with 5% KHSO$_4$, NaCl-saturated water, a saturated solution of NaHCO$_3$ and, once again, with NaCl-saturated water, and then dried with Na$_2$SO$_4$. The solvent was removed in vacuo. The crude product was used directly, without further purification, for the next step in the synthesis.

Yield: 3.7 g (crude product), HPLC: 61.84% B

3e) Bzls-D-Cha-Lys-4-(Amidino)benzylamide×2 HBr 3.5 g of Bzls-D-Cha-Lys(Z)-4-(acetyloxamidino)-benzylamide (crude product) were dissolved in 175 ml of 90% acetic acid after which 400 mg of catalyst (10% Pd/C) were added. The mixture was hydrogenated with hydrogen for 6 h at room temperature and under standard pressure. The catalyst was then filtered off and the solvent was evaporated off; toluene was added to the residue and the solvent was evaporated off again in vacuo. 50 ml of hydrogen (33% strength in acetic acid) were added to the residue; the mixture was shaken occasionally. After an hour, the product was precipitated by adding diethyl ether, filtered off with suction and washed several times with diethyl ether. The resulting solid (faintly yellowish) was dried in vacuo. The crude product was used for the next step in the synthesis.

Yield: 2.3 g of crude product, HPLC: 34.77% B.

Part of the crude product was purified by means of preparative reversed-phase HPLC.

MS: calculated 584.31 (monoisotopic). found 585.4 [M+H]$^+$.

3f) Bzls-D-Cha-Lys (CO—CH$_2$—O—CH$_2$—CO—NH—CH$_2$—CH$_2$-Hexaethylene glycol-CH$_2$—CH$_2$—NH-Boc)-4-(amidino)benzylamide×HBr 0.318 g (approx. 0.427 mmol) of Bzls-D-Cha-Lys-4-(amidino)benzylamide×2 HBr crude product and 250 mg (0.4275 mmol) of O—(N-Boc-2-aminoethyl)-O'—(N-diglycolyl)-2-aminoethyl)hexaethylene glycol (Novabiochem, order no.: 01-63-0102) were dissolved in 10 ml of DMF. While cooling with ice, 0.222 g (0.4275 mmol) of PyBop and 149 µl (0.855 mmol) of DIEA were added. The mixture was stirred for 15 min while being cooled with ice and for a further 4 h at room temperature. After that, the solvent was evaporated off in vacuo and the residue was taken up in approx. 350 ml of ethyl acetate and 75 ml of a saturated solution of NaHCO$_3$. The ethyl acetate phase was washed once again with a saturated solution of NaHCO$_3$ and then 2× with a saturated solution of NaCl; it was then dried with Na$_2$SO$_4$. The solvent was removed in vacuo, resulting in a yellow oil which was used without further purification for the next step in the synthesis.

Yield: 446 mg, HPLC: 47.03% B

Part of the compound was purified by means of preparative HPLC.

3g) Bzls-D-Cha-Lys (CO—CH$_2$—O—CH$_2$—CO—NH—CH$_2$—CH$_2$-hexaethylene glycol-CH$_2$—CH$_2$—NH$_2$)-4-(amidino)benzylamide×2 TFA 10 ml of 1 N HCl in acetic acid were added to 400 mg of compound 3f (Bzls-D-Cha-Lys (CO—CH$_2$—O—CH$_2$—CO—NH—CH$_2$—CH$_2$-hexaethylene glycol-CH$_2$—CH$_2$—NH-Boc)-4-(amidino)benzylamide×HBr crude product). After an hour at room temperature, the product was precipitated by adding diethyl ether, filtered off with suction and purified by means of preparative HPLC.

Yield: 210 mg, HPLC: 37.2% B

MS: calculated 1050.57 (monoisotopic). found 1051.6 [M+H]$^+$.

EXEMPLARY EMBODIMENT 4

Synthesizing benzylsulfonyl-D-Cha-Glu (NH—[CH$_2$]$_3$—[O—CH$_2$—CH$_2$]$_2$—O—[CH$_2$]$_3$—NH$_2$)-4-Amba×2 TFA

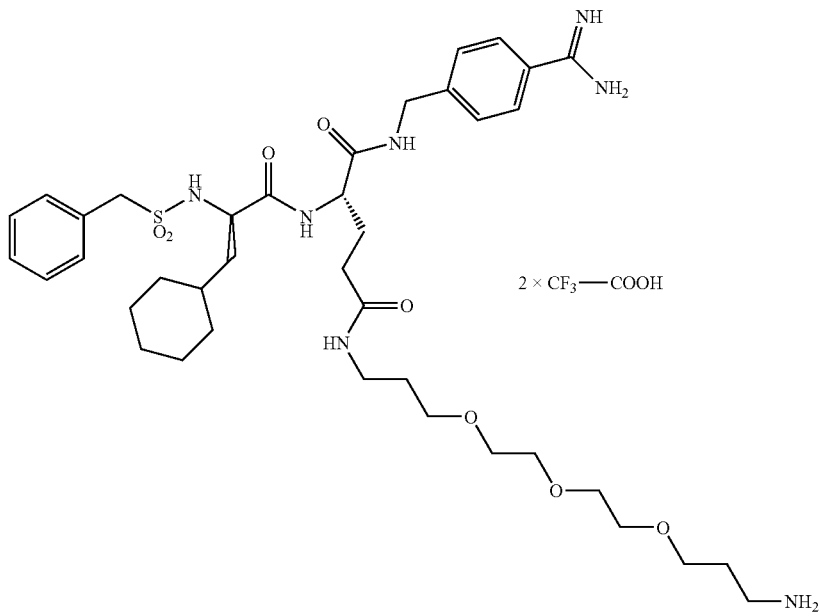

4a)
Boc-Glu(OBzl)-4-(Acetyloxamidino)benzylamide 3.37 g (10 mmol) of Boc-Glu(OBzl)-OH were dissolved in 100 ml of DMF after which 1.1 ml (10 mmol) of NMM and 1.3 ml (10 mmol) of IBCC were added. The mixture was stirred at −15° C. for 8 min after which 2.44 g (10 mmol) of 4-(acetyloxamidino)benzylamine×HCl (prepared as described in WO 01/96286 A2) and, once again, 1.1 ml (10 mmol) of NMM were added. The mixture was stirred for a further hour at −15° C. and overnight at room temperature. The solvent was removed in vacuo and the mixture was taken up in ethyl acetate; this solution was then washed, in each case 3×, with 5% $KHSO_4$, NaCl-saturated water, a saturated solution of $NaHCO_3$ and, once again, with NaCl-saturated water and then dried with $Na_2SO_4$. The solvent was removed in vacuo and the compound was crystallized from ethyl acetate.

Yield: 3.8 g (7.2 mmol), HPLC: 52.34% B

4b) H-Glu(OBzl)-4-(Acetyloxamidino)benzylamide×HCl 80 ml of 1 N HCl in glacial acetic acid were added to 3 g (6 mmol) of Boc-Glu(OBzl)-4-(acetyloxamidino)benzylamide. After the mixture had been standing at room temperature for 45 min, the solvent was partially evaporated off and the product was precipitated by adding diethyl ether, filtered off with suction and washed once again with diethyl ether. The product was dried in vacuo.

Yield: 2.5 g (5.4 mmol) of white solid, HPLC: 31.07% B

4c) Bzls-D-Cha-Glu(OBzl)-4-(Acetyloxamidino)benzylamide 0.84 g (2.59 mmol) of Bzls-D-Cha-OH and 1.2 g (2.59 mmol) of H-Glu(OBzl)-4-(acetyloxamidino)benzylamide×HCl were dissolved in 40 ml of DMF after which 1.35 g (2.59 mmol) of PyBop and 1.35 ml (7.77 mmol) of DIEA were added at 0° C. The mixture was stirred for 30 min at 0° C. and for a further 4 h at room temperature. The solvent was removed in vacuo and the residue was taken up in ethyl acetate; this solution was then washed, in each case 3×, with 5% $KHSO_4$, NaCl-saturated water, a saturated solution of $NaHCO_3$ and, once again, with NaCl-saturated water, after which it was dried with $Na_2SO_4$. The solvent was removed in vacuo.

Yield: 1.35 g (oil), HPLC: 63.16% B

4d) Bzls-D-Cha-Glu-4-(Amidino)benzylamide×HCl 1.2 g of Bzls-D-Cha-Glu(OBzl)-4-(acetyloxamidino)-benzylamide were dissolved in 200 ml of 90% acetic acid after which 200 mg of catalyst (10% Pd/C) were added. The mixture was hydrogenated with hydrogen for 24 h at 45° C. and under standard pressure. The catalyst was then filtered off and the solvent was evaporated off; toluene was added to the residue and the solvent was evaporated off once again in vacuo. The residue was dissolved in 25 ml of a 1 N solution of HCl in glacial acetic acid and the product was precipitated by adding diethyl ether, filtered off with suction and washed several times with diethyl ether. The resulting solid was dried in vacuo.

Yield: 0.82 g, HPLC: 40.55% B.

A part of the crude product was purified by means of preparative reversed-phase HPLC.

MS: calculated 585.26 (monoisotopic). found 586.5 $[M+H]^+$.

4e) Bzls-D-Cha-Glu (NH—$[CH_2]$3-[O—$CH_2$—$CH_2]_2$—O—$[CH_2]_3$—NH-Boc)-4-(Amidino)benzylamide×HCl 0.4 g (0.643 mmol) of Bzls-D-Cha-Glu-4-(amidino)benzylamide×HCl and 0.216 g (0.675 mmol) of Boc-NH—$(CH_2)_3$—O—$CH_2$—$CH_2)_2$—O—$(CH_2)_3$—$NH_2$ (obtained from Quanta Biodesign, Powell, Ohio) were dissolved in 10 ml of DMF after which 0.335 g (0.643 mmol) of PyBop and 224 μl (1.29 mmol) of DIEA were added at 0° C. The mixture was stirred for 30 min at 0° C. and for a further 6 h at room temperature. The solvent was removed in vacuo and the residue was taken up in a mixture of ethyl acetate and a saturated solution of $NaHCO_3$. The mixture was shaken in a separating funnel and the alkaline phase was separated off. The ethyl acetate phase was washed once again with a saturated solution of $NaHCO_3$. The ethyl acetate was removed in vacuo and the remaining residue was used without purification for the next step in the synthesis.

Yield: 0.35 g (oil), HPLC: 49.17% B

4f) Bzls-D-Cha-Glu (NH—$[CH_2]_3$—[O—$CH_2$—$CH_2]_2$—O—$[CH_2]_3$—$NH_2$)-4-(Amidino)benzylamide×2 TFA 20 ml of 1 N HCl in glacial acetic acid were added to the crude product of compound 4e (Bzls-D-Cha-Glu(NH—$[CH_2]_3$—[O—$CH_2$—$CH_2]_2$—O—$[CH_2]_3$—NH-Boc)-4-(amidino)benzylamide×HCl). The mixture was left to stand for 45 min and, after that, the product was precipitated by adding diethyl ether and filtered off with suction. The resulting solid was purified by means of preparative reversed-phase HPLC and the product was lyophilized.

Yield: 0.21 g of lyophilisate, HPLC: 36.33% B

MS: calculated 787.43 (monoisotopic). found 788.5 $[M+H]^+$.

EXEMPLARY EMBODIMENT 5

Determining the Inhibitory Constants ($K_i$ Values in μM)

The inhibitory effect for the individual enzymes was determined in analogy with a method which has already been described (Stürzebecher et al., J. Med. Chem. 40, 3091-3099, 1997).

Specifically for determining the inhibition of PK, 200 μl of Tris buffer (0.05 M, 0.154 M NaCl, 5% ethanol, pH 8.0; contains the inhibitor), 50 μl of substrate (Bzl-Pro-Phe-Arg-pNA in $H_2O$) and 25 μl of PK were incubated at 25° C. After 3 min, the reaction was terminated by adding 25 μl of acetic acid (50%) and the absorption at 405 μm was determined using a Microplate Reader (Labsystems iEMS Reader MF). The $K_i$ values were determined, in accordance with Dixon (Biochem. J. 55, 170-171, 1953), by means of linear regression and using a computer program. The $K_i$ values are the mean of at least three determinations.

The inhibition of factor XIa and factor XIIa was determined in an analogous manner. When determining the inhibitory constants for human factor XIa (Haemochrom Diagnostica GmbH, Essen, Germany), H-D-Lys(Z)-Pro-Arg-pNA (Chromozym PCa, Roche Diagnostics GmbH, Mannheim, Germany) was used as the substrate.

H-D-HHT-Gly-Arg-pNA (Chromozym XII, Roche Diagnostics GmbH, Mannheim, Germany) was used as the substrate for measuring the inhibitory constants of human factor XIIa (Haemochrom Diagnostica GmbH, Essen, Germany).

TABLE 1

Inhibition of PK, factor XIIa, factor XIa and thrombin by compounds of the (R)-benzylsulfonyl-D-Ser-Aaa-4-Amba type

| | | | $K_i$, µM | | | |
|---|---|---|---|---|---|---|
| No. | Aaa | R | PK | F XIIa | F XIa | Thrombin |
| 1 | Gly | H | 1.7 | 16 | 2.2 | 13 |
| 2 | Ala | H | 0.070 | 9.2 | 0.11 | 0.11 |
| 3 | Pro | H | 0.054 | 5.1 | 0.10 | 0.012 |
| 4 | Asp | H | 3.7 | >1000 | n.d. | >1000 |
| 5 | Glu | H | 1.1 | >1000 | n.d. | 38 |
| 6 | Gln | H | 0.047 | 25 | 0.13 | 0.49 |
| 7 | hGlu | H | 20 | >1000 | 11 | >1000 |
| 8 | Dap | H | 0.050 | 15 | 0.39 | 0.65 |
| 9 | Dap(Z) | H | 0.042 | 13 | 0.28 | 6.9 |
| 10 | Lys | H | 0.016 | 21 | 0.89 | 4.3 |
| 11 | Lys(Z) | H | 0.0035 | 15 | 0.3 | 0.18 |
| 12 | Arg | H | 0.079 | 16 | 0.77 | 4.7 |
| 13 | Thr | H | 0.24 | 51 | 0.25 | 4.0 |
| 14 | Thr(Bzl) | H | 0.091 | 23 | 0.33 | 0.30 |
| 15 | Ser | H | 0.16 | 80 | 0.30 | 14 |
| 16 | Ser(Bzl) | H | 0.025 | 9.8 | 0.30 | 0.48 |
| 17 | hSer | H | 0.020 | >1000 | n.d. | 8.5 |
| 18 | Phe | H | 0.021 | 0.97 | 0.92 | 1.6 |
| 19 | hPhe | H | 0.048 | 2.8 | 0.084 | 1.2 |
| 20 | Gly | 4-COOH | 0.70 | >1000 | 0.60 | 170 |
| 21 | Gly | 4-COOMe | 4.2 | 42 | 8.1 | 9.4 |
| 22 | Ala | 4-COOH | 0.016 | 17 | 0.015 | 2.3 |
| 23 | Ser | 4-COOH | 0.029 | >1000 | 0.17 | 120 |
| 24 | Ser | 4-COOMe | 0.16 | 19 | 0.87 | 4.2 |
| 25 | Gly | 4-AMe | 6.3 | 17 | 6.0 | 8.0 |

TABLE 2

Inhibition of PK, factor XIIa, factor XIa and thrombin by compounds of the (R)-benzylsulfonyl-D-Ser(tBu)-Aaa-4-Amba type

| | | | $K_i$, µM | | | |
|---|---|---|---|---|---|---|
| No. | Aaa | R | PK | F XIIa | F XIa | Thrombin |
| 26 | Gly | H | 0.34 | 2.6 | 1.4 | 0.22 |
| 27 | Ala | H | 0.061 | 2.0 | 0.030 | 0.0021 |
| 28 | Pro | H | 0.0065 | 0.49 | 0.036 | 0.0020 |
| 29 | Asp | H | 0.91 | >1000 | 0.39 | 6.0 |
| 30 | Glu | H | 0.36 | 19 | 0.079 | 2.6 |
| 31 | Gln | H | 0.0092 | 6.3 | 0.067 | 0.021 |
| 32 | hGlu | H | 8.0 | >1000 | 8.2 | >1000 |
| 33 | Dap | H | 0.022 | 4.0 | 0.19 | 0.0094 |
| 34 | Dap(Z) | H | 0.025 | 0.93 | 0.31 | 0.37 |
| 35 | Lys | H | 0.0036 | 4.4 | 0.51 | 0.055 |
| 36 | Lys(Z) | H | 0.0094 | 5.4 | 0.48 | 0.024 |
| 37 | Arg | H | 0.040 | 2.6 | 0.34 | 0.065 |
| 38 | Thr | H | 0.032 | 14 | n.d. | 0.044 |
| 39 | Thr(Bzl) | H | 0.044 | 17 | 0.40 | 0.019 |
| 40 | Ser | H | 0.052 | 6.0 | 0.20 | 0.047 |
| 41 | Ser(Bzl) | H | 0.012 | 1.4 | 0.20 | 0.012 |
| 42 | hSer | H | 0.21 | >1000 | 0.74 | 13 |
| 43 | hSer(Bzl) | H | 0.0082 | 80 | 0.61 | 0.50 |
| 44 | Phe | H | 0.0055 | 4.6 | 0.26 | 0.16 |
| 45 | hPhe | H | 0.0045 | 1.3 | 0.083 | 0.048 |
| 46 | Gly | 4-COOH | 0.029 | 7.5 | n.d. | 2.2 |
| 47 | Gly | 4-COOMe | 1.1 | 4.8 | 1.6 | 0.36 |
| 48 | Ala | 4-COOH | 0.0062 | 9.5 | 0.0069 | 0.044 |
| 49 | Ala | 4-COOMe | 0.054 | 4.7 | 0.079 | 0.0043 |
| 50 | Gly | 4-AMe | 4.0 | 1.8 | 2.9 | 0.12 |
| 51 | Pro | 4-CN | 0.0094 | 1.6 | 0.0091 | 0.000064 |

TABLE 3

Inhibition of PK, factor XIIa, factor XIa and thrombin by compounds of the (R)-benzylsulfonyl-D-Cha-Aaa-4-Amba type

| | | | $K_i$, µM | | | |
|---|---|---|---|---|---|---|
| No. | R | Aaa | PK | F XIIa | F XIa | Thrombin |
| 52 | 3-CN | Pro | 0.086 | 13 | n.d. | <0.0010 |
| 53 | H | Lys | 0.0023 | 0.83 | 0.15 | 0.010 |
| 54 | H | Lys(Z) | 0.020 | 4.0 | 0.34 | 0.015 |
| 55 | 3-AMe | Pro | 0.090 | 0.47 | 0.17 | 0.0032 |
| 56 | 3-(Glut-NHCH$_2$) | Pro | 0.044 | 5.6 | 0.052 | <0.0010 |
| 57 | H | Glu | 0.030 | 4.0 | 0.020 | 0.081 |

Inhibitory constants for PEG-coupled compounds in µM:
Inhibitor No. 58:

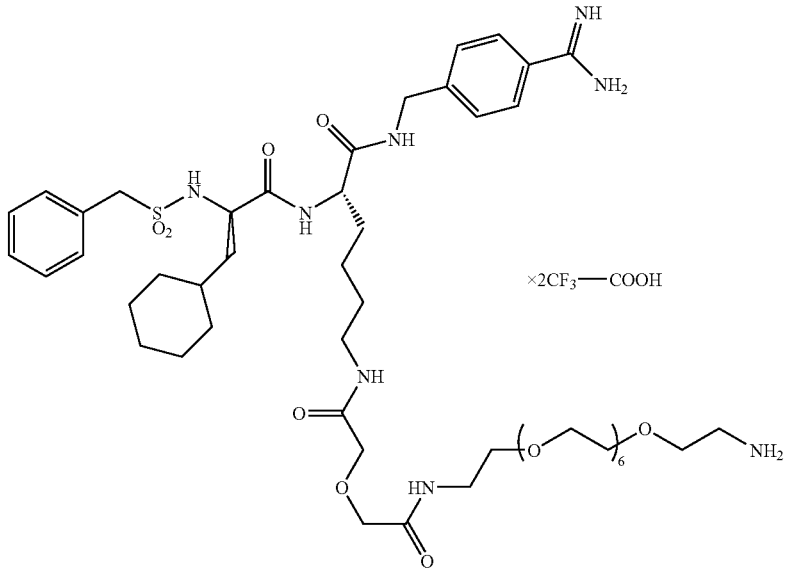

PK 0.059; F XIIa 2.0, F XIa 0.23, thrombin 0.0080

Inhibitor No. 59:

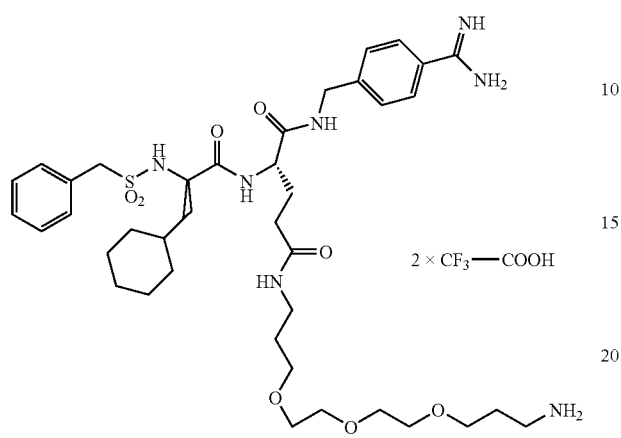

PK 0.015; F XIIa 0.98, F XIa 0.040, thrombin 0.015

TABLE 4

Inhibition of PK, factor XIIa, factor XIa and thrombin by compounds of the (4-R)-benzylsulfonyl-P3-Aaa-4-Amba type ((4-R) denotes the 4 position of the radical R in Table 4 on the phenyl ring of the benzylsulfonyl radical)

| | | | | $K_i$, µM | | | |
|---|---|---|---|---|---|---|---|
| No. | R | P3 | Aaa | PK | F XIIa | F XIa | Thrombin |
| 60 | H | D-hAla(4-Pyr) | Glu(OBzl) | 0.0055 | 0.094 | 0.031 | 0.17 |
| 61 | COOH | D-Ser | Pro | 0.0091 | 29 | 0.014 | 0.24 |
| 62 | H | D-Ser(tBu) | Lys(Tfa) | 0.011 | 6.1 | n.d. | 0.0029 |
| 63 | H | D-Cha | Gly | 0.011 | 0.70 | 25 | 0.0090 |
| 64 | H | D-Ser(tBu) | His | 0.014 | 61 | n.d. | 0.12 |
| 65 | COOH | D-Ser(tBu) | Ser | 0.015 | 17 | 0.030 | 2.0 |
| 66 | CH$_2$COOH | D-Ser(tBu) | Pro | 0.016 | 4 | n.d. | 0.0018 |
| 67 | H | D-hPhe | Ser | 0.019 | 0.63 | 3.0 | 0.55 |
| 68 | H | D-Ser(tBu) | Can | 0.019 | 6.8 | n.d. | 0.038 |
| 69 | H | D-hAla(4-Pyr) | Ser | 0.020 | 1.6 | n.d. | 0.91 |
| 70 | COOH | D-Ser(tBu) | Pro | 0.025 | 2.4 | n.d. | 0.0023 |
| 71 | H | D-Cha | Lys(Suc) | 0.029 | 11 | n.d. | 0.0021 |
| 72 | H | D-hTyr | Glu | 0.22 | 0.36 | 0.028 | 19 |
| 73 | H | D-hTyr | Ser | 0.13 | 0.28 | 0.078 | 1.4 |
| 74 | NO$_2$ | D-hPhe | Gly | 0.051 | 0.39 | 0.093 | 0.71 |
| 75 | H | D-hTyr | Gly | 0.12 | 0.78 | 0.61 | 1.5 |
| 76 | H | D-hPhe | Gly | 0.39 | 0.15 | 0.27 | 0.047 |
| 77 | H | D-Phe(3-amidino) | Gly | 0.082 | 0.19 | 0.25 | 0.085 |
| 78 | NH$_2$ | D-hPhe | Gly | 0.045 | 0.26 | 0.12 | 0.26 |
| 79 | H | D-Phe(3-GuMe) | Gly | 0.075 | 0.31 | 0.22 | 0.059 |
| 80 | H | D-norarginine | Gly | 0.068 | 0.34 | 0.49 | 2.1 |
| 81 | H | D-Arg | Gly | 0.074 | 0.35 | 0.70 | 1.4 |
| 82 | H | D-Cha | Gly | 0.10 | 1.4 | 0.33 | 0.023 |
| 83 | H | D-indanylglycine | Gly | 0.075 | 0.37 | n.d. | 0.14 |
| 84 | COOCH$_3$ | D-Phe(3-amidino) | Gly | 0.14 | 0.38 | 0.70 | 0.53 |
| 85 | H | D/L-hAla(4-Pyr) | Gly | 0.13 | 0.40 | 1.1 | 2.0 |
| 86 | H | D-Ser | Lys(Glut) | 0.39 | n.d. | n.d. | 2.8 |

Inhibitor 87:

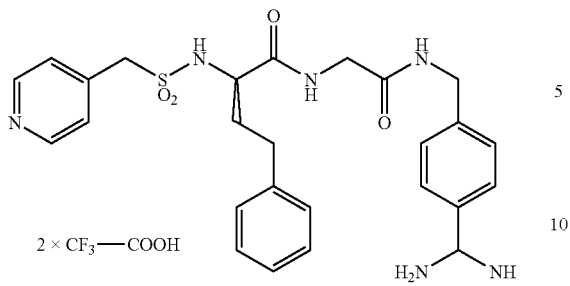

$K_i$ values in μM: PK 0.42; F XIIa 0.16; F XIa 0.33, thrombin 3.6

Inhibitor 88

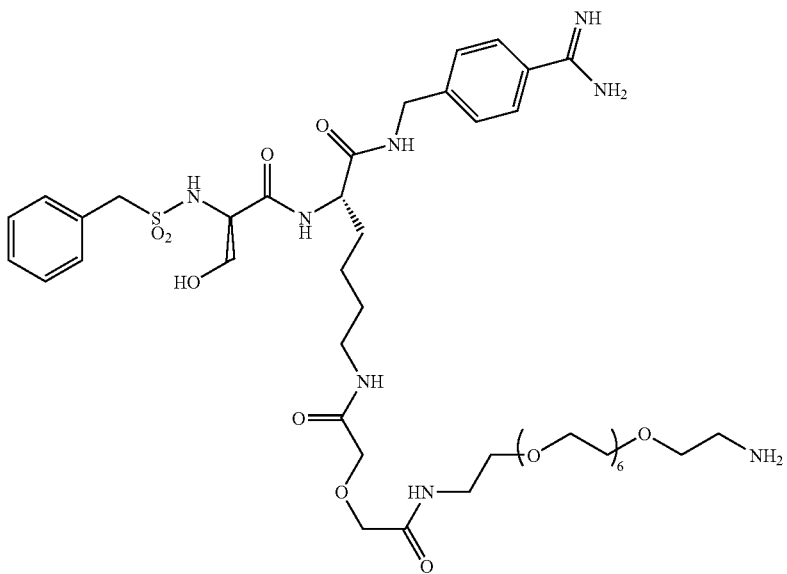

$K_i$ values in μM: PK 0.22; F XIIa 21; F XIa 0.4, thrombin 1.2

Inhibitor 89

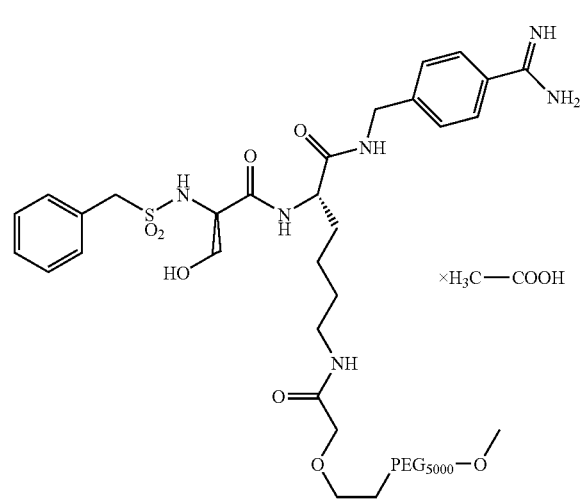

$K_i$ values in μM: PK 0.19; F XIIa 79; thrombin 1.72. PEG$_{5000}$ denotes a polyethylene glycol having an average molecular weight of 5000 daltons.

EXEMPLARY EMBODIMENT 6

Preventing the Activation of Prothrombin in Hirudin-Anticoagulated Plasma

Venous blood from healthy voluntary donors was mixed, immediately after removal, with hirudin solution (2000 ATU/ml, 0.9% NaCI solution) in a ratio of 10:1 and this mixture was centrifuged at 250×g for 10 min. 950 μl of plasma were mixed with 20 μl of inhibitor solution (5 or 0.5 mM) and incubated at 37° C., for 5 h in polypropylene tubes. 30 μl of kaolin (PTT reagent, diluted 1:1000; Roche Diagnostics, Penzberg, Germany) were added in order to augment the activation at the synthetic surface.

An enzyme immunoassay (Enzygnost-F 1+2, DadeBehring GmbH, Marburg, Germany) in accordance with the Sandwich principle was used for determining the prothrombin fragment F 1+2. The prothrombin fragment binds to fixed antibodies directed against F 1+2. Peroxidase-conjugated antibodies directed against prothrombin bind in a second step and the bound enzyme activity is determined chromogenically. The concentration of prothrombin fragment F 1+2 was ascertained from a calibration curve.

TABLE 5

Influence of different compounds on the activation of prothrombin in hirudin-anticoagulated plasma in polypropylene tubes in the added presence of kaolin. The quantity of the prothrombin fragment F 1 + 2 (in nM) which was detected after 5 h in the presence of kaolin was set at 100%.

| Inhibitor no. | Prothrombin fragment F 1 + 2 (%) | | | | |
|---|---|---|---|---|---|
| | +kaolin | −kaolin | Kaolin + inhibitor 100 µM | Kaolin + inhibitor 10 µM | Kaolin + inhibitor 1 µM |
| 45 | 100 | 0.64 | 0.11 | 0.59 | n.d. |
| 11 | 100 | 0.49 | 0.15 | 110.9 | n.d. |
| 53 | 100 | 0.46 | 0.08 | 0.09 | 0.59 |
| 59 | 100 | 0.46 | 0.03 | 0.20 | 59.3 |
| 75 | 100 | 0.14 | n.d. | 0.01 | 0.07 |
| 73 | 100 | 0.14 | n.d. | 0.04 | 0.07 |

EXEMPLARY EMBODIMENT 7

Use of a PK Inhibitor for Affinity Chromatography as a Model for Modifying a Synthetic Surface The material for an affinity chromatography was prepared by coupling the inhibitor benzylsulfonyl-D-Ser-Lys-4-Amba to CH-Sepharose 4B (Pharmacia). For this, 16 g of swollen CH-Sepharose 4B were first of all suspended in 65 ml of MES buffer (0.1 M, pH 4.75) after which the inhibitor (50 mg in 2 ml of buffer) was added. 2.837 g of N-cyclohexyl-N'-(2-morpholino-ethyl)carbodiimide metho-p-toluenesulfonate (Acros Organics) were added to the mixture (corresponds to 0.1 M in the mixture) and the whole was incubated at room temperature for 24 h. The Sepharose was then washed with MES buffer and water and equilibrated with Tris buffer (0.05 M, contains 0.75 M NaCl, pH 7.5). After the column (1.4×19 cm) had been packed and equilibrated, 100 µg of PK (Haemochrom Diagnostics, Essen, Germany) were loaded on in 1 µl of buffer. The column was then washed firstly with Tris buffer and then with a 3 M NaCl solution, with no PK being eluted in this connection. 41% active PK was eluted by means of a subsequent benzamidine gradient (0.1-2.5 M).

A comparable result can be obtained when using an affinity chromatography column in which the inhibitor depicted below is coupled on covalently.

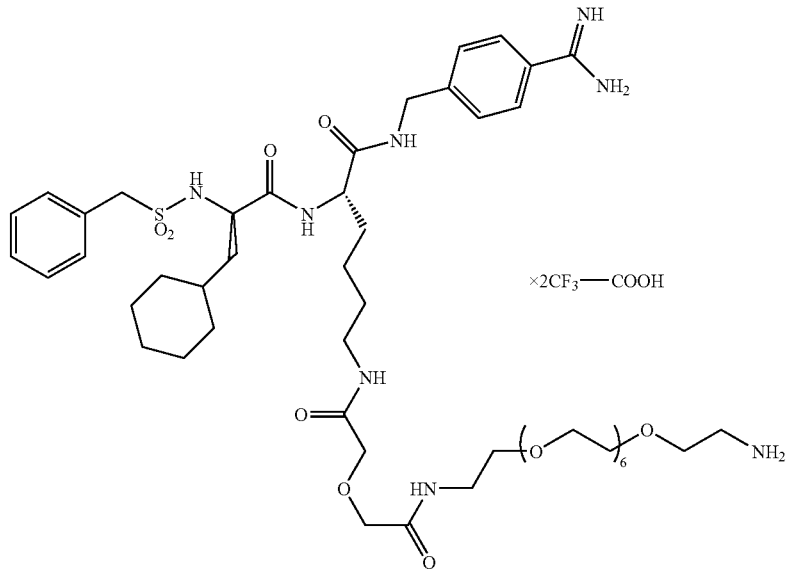

The invention claimed is:

1. A method of inhibiting plasma kallikrein and/or factor XIa and/or factor XIIa in-a patient having a condition selected from the group consisting of cardiac infarction, an embolism, deep leg vein thrombosis, unstable angina, complications as a consequence of angioplasty, disseminated intravascular coagulation, septic shock, allergies, postgastrectomy syndrome, and adult respiratory distress syndrome, said method comprising administering to said patient a compound of formula I:

wherein
P1 is unsubstituted 4-amidinobenzylamine; and
(1) P4 is unsubstituted benzylsulfonyl,
P3 is D-Ser or D-Ser(tBu), and
P2 is Asp, Glu, Gln, hGlu, Dap(Z), Lys(Z), Thr, Thr (Bzl), Ser, Ser(Bzl), hSer, Phe or hPhe;
(2) P4 is benzylsulfonyl substituted with 4-COON or 4-COOMe,
P3 is D-Ser, and
P2 is Ser;
(3) P4 is benzylsulfonyl substituted with 4-CN,
P3 is D-Ser, and
P2 is Pro;
(4) P4 is unsubstituted benzylsulfonyl,
P3 is D-Cha, and
P2 is Glu, Lys, or Lys(Z); or
(5) P4 is benzylsulfonyl substituted with 3-CN, 3-aminomethyl, or 3-(Glut-NHCH$_2$),
P3 is D-Cha, and
P2 is Pro;
wherein the sulfur atom of the benzylsulfonyl group of P4 is linked to the α-amino group of P3, the carbon atom of the carbonyl group of P3 is bonded to the α-amino group of P2 or, when P2 is hSer, to the β-amino group of P2, and
the nitrogen atom of benzylamine of P1 is linked to the C-terminal carbonyl group of P2.

2. The method of claim 1, wherein P4 is unsubstituted benzylsulfonyl.

3. The method of claim 2, wherein P3 is D-Ser.

4. The method of claim 3, wherein P2 is hPhe.

5. The method of claim 1, wherein said compound is administered enterally.

6. The method of claim 5, wherein said compound is administered orally.

7. The method of claim 1, wherein said compound is administered parenterally.

8. The method of claim 7, wherein said compound is administered intraarterially, intravenously, intramuscularly, or subcutaneously.

9. The method of claim 1, wherein said deep leg vein thrombosis follows a hip joint surgery or a knee joint replacement.

10. The method of claim 1, wherein said angioplasty is percutaneous transluminal coronary angioplasty.

* * * * *